United States Patent [19]

Kauffman

[11] 4,439,730
[45] Mar. 27, 1984

[54] NONDESTRUCTIVE INSPECTION APPARATUS AND METHOD UTILIZING COMBINED INSPECTION SIGNALS OBTAINED FROM ORTHOGONAL MAGNETIC FIELDS

[75] Inventor: Glenn A. Kauffman, Pasadena, Tex.

[73] Assignee: AMF Inc., White Plains, N.Y.

[21] Appl. No.: 261,918

[22] Filed: May 8, 1981

[51] Int. Cl.³ ............... G01N 27/72; G01R 33/12; G09F 9/30
[52] U.S. Cl. .............................. 324/232; 340/703; 340/715
[58] Field of Search ............... 324/228, 232, 233–243, 324/262, 226; 340/703, 704, 715, 324 R

[56] References Cited

U.S. PATENT DOCUMENTS

| | | | |
|---|---|---|---|
| 3,582,771 | 6/1971 | Placke | 324/226 |
| 3,612,987 | 10/1971 | Placke et al. | 324/242 |
| 3,849,793 | 11/1974 | Ablett | 340/324 R X |
| 3,906,357 | 9/1975 | Runshang | 324/226 |
| 4,016,544 | 4/1977 | Morita et al. | 340/703 X |
| 4,020,501 | 4/1977 | Hillberger et al. | 340/703 X |
| 4,379,292 | 4/1983 | Minato et al. | 340/703 X |

Primary Examiner—Gerard R. Strecker
Assistant Examiner—Warren S. Edmonds
Attorney, Agent, or Firm—David E. Dougherty; John H. Gallagher

[57] ABSTRACT

Method and apparatus for nondestructively testing each incremental area of a ferromagnetic sample by first passing a steady magnetic flux field through an area in a first direction and producing an inspection signal in response thereto, and then passing a steady magnetic flux field through the same area in an orthogonal direction and producing a second inspection signal in response thereto. The magnitudes of the two inspection signals corresponding to a given incremental area are added to produce a composite signal whose magnitude is the sum of the two signals. The composite signal associated with a given incremental region is displayed on a visual presentation means at a location corresponding to the location of the incremental region on the ferromagnetic sample and with an indicia, such as color, that is a function of the magnitude of the respective composite signal.

36 Claims, 23 Drawing Figures

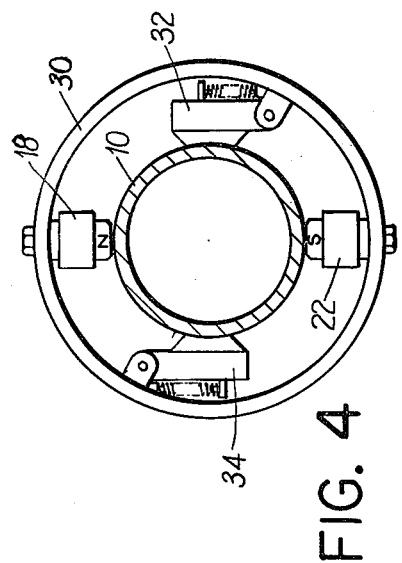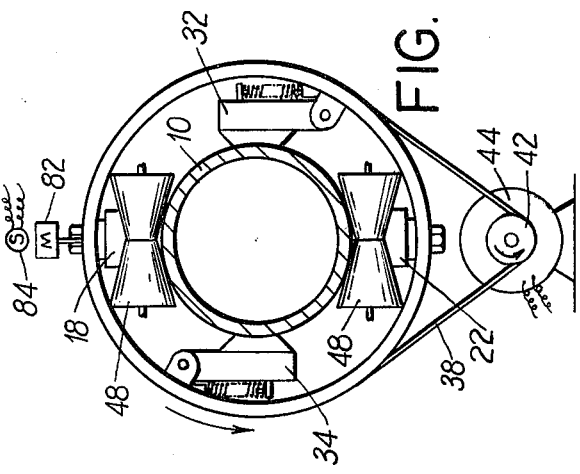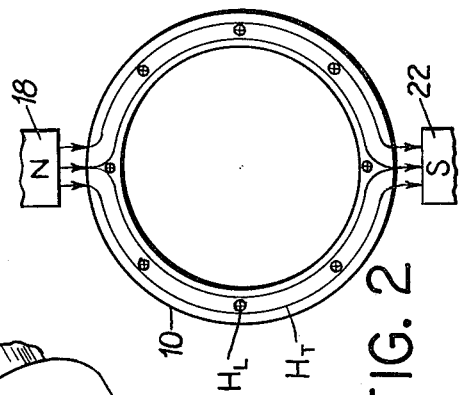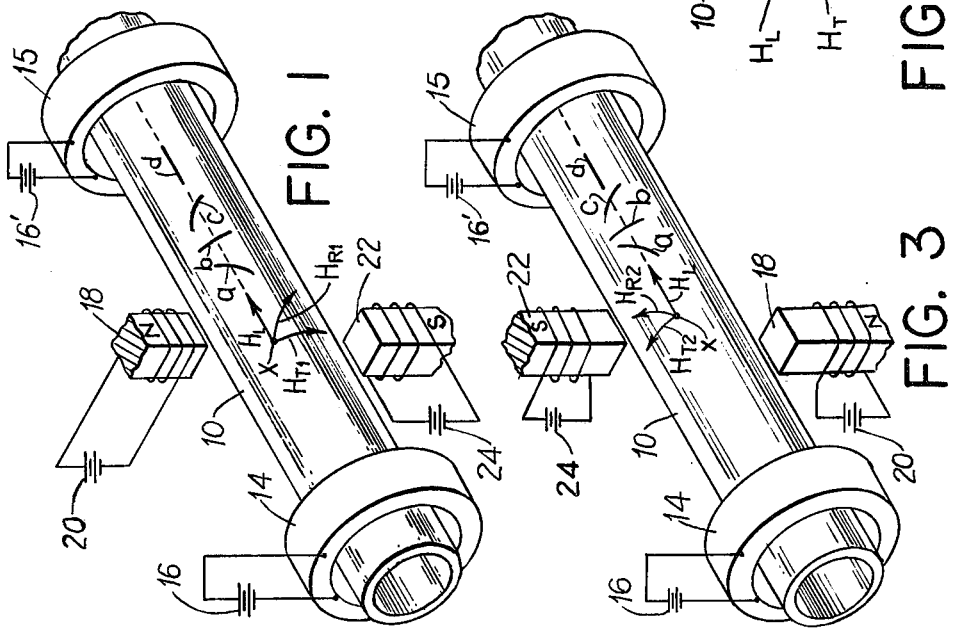

NONDESTRUCTIVE INSPECTION APPARATUS AND METHOD UTILIZING COMBINED INSPECTION SIGNALS OBTAINED FROM ORTHOGONAL MAGNETIC FIELDS

This invention relates to nondestructive inspection, and more particularly to the magnetic flux leakage inspection of elongated tubular goods and to the visual presentation of inspection signals.

The nondestructive inspection of ferromagnetic objects by the technique of magnetic flux leakage detection is an old and well developed art. As presently practiced, a steady, unidirectional magnetic flux field is established in the wall of the pipe, for example, that is being inspected. If there are no anomalies in the pipe wall the flux will flow largely within the wall of the pipe between its entrance and exit regions. A minor portion of the flux will be present outside the pipe wall. If a physical or metallurgical anomaly exists in the portion of the pipe wall in which the flux field is established, the lines of flux will bridge around, or be drawn into, the anomaly depending on its nature. In any event, the lines of flux outside the pipe wall and adjacent the anomaly will be increased or decreased in density and/or extent. When a magnetic flux responsive detector is passed along the pipe wall it will encounter the change in the external flux field due to the anomaly and will produce a corresponding electrical signal. The flux responsive device may be a wire coil, a magneto diode, or a Hall effect device or generator, for example.

The flux leakage inspection method described above has an inherent limitation that has long been a problem and a detriment to achieving desired excellence in detecting anomalies, especially anomalies that are elongated and narrow. When a long, narrow anomaly such as a crack extends parallel to the lines of magnetic flux the flux lines within the sample merely pass to the sides of the crack and are disturbed to a minimum extent. Correspondingly, the external flux field is disturbed to a minimum extent and a flux responsive detector that is passed along the surface will produce a minimal change of signal, if at all. On the other hand, if the long narrow crack extends perpendicularly to the direction of the magnetic flux lines it will have optimum effect to disturb the flow of magnetic flux and will cause optimum external fringing, bridging, or the like, of the flux lines. Under these conditions the flux responsive device that passes along the surface and across the crack will produce an optimum change of signal.

Because of the above-described inherent limitation in the flux leakage inspection method it has become customary to subject a length of pipe to two simultaneous but independent flux leakage inspections. In the first one, a longitudinally directed steady magnetic field is established throughout the entire circumference of a section of the pipe and magnetic flux responsive detectors are disposed circumferentially around the pipe in the region of the longitudinal field. Relative longitudinal motion is established between the pipe and detectors. Any anomaly in the pipe wall that has a significant circumferential extent will disturb the flow of the longitudinally directed flux lines and will cause the so-called flux leakage externally of the pipe wall. As the detectors pass across or through the leakage flux they produce a signal.

The second inspection unit is axially spaced along the pipe from the first unit and a steady magnetic field is directed transversely across the pipe. The magnetic flux flows circumferentially in two paths around opposite 180° segments of the pipe wall, or primarily through only a single angular segment of the circumference, depending on the positions of the magnetic pole pieces of the magnetizing source. Flux leakage detectors are disposed adjacent the pipe wall in the region of the transverse field and relative circumferential motion is established therebetween. Circumferentially extending cracks will have a minimal effect on the circumferentially flowing flux lines and the detectors will produce little or no signal. A longitudinally extending crack will intercept the flux lines to an optimum extent and will cause appreciable flux leakage that will be detected by a detector as it passes by.

In both of the inspection units described above multiple flux leakage detector means were employed. In both units, the multiple detectors were so arranged and the relative motion between the pipe and the detectors was so selected that the inspection coverages of the pipe surface by the detectors was interlaced with only enough overlap of the inspection coverages of adjacent detectors so as to assure that 100% coverage of the pipe surface was accomplished. As far as I am aware, adjacent search shoes never inspected exactly the same surface area of the pipe wall. In all prior art systems that I am aware of each search shoe covers a respective portion of the pipe's surface during its relative motion, and it is required that the coverage of all the search shoes be combined or interlaced in order to achieve 100% inspection coverage of the pipe.

Inspection apparatus that performs the two types of inspections described above is described in U.S. Pat. No. 3,906,357 issued Sept. 16, 1975, to A. Runshang.

Because the two inspection operations described above were carried out independently it was not always easy for the operator of the equipment to interpret the separate inspection results or to correlate the inspection results with each other. The inspection results usually are recorded on a pen and ink strip chart recorder with the anomalies appearing as spikes or pulses on the strip chart. From the chart it is difficult and sometimes impossible to determine the type of flaw that caused the spike or pulse, its orientation, or its area size or depth. It is possible that a severe anomaly that was not precisely perpendicular to a particular steady magnetizing field might appear on the strip chart as a small or marginally acceptable anomaly. Further, an acceptable shallow pit of large area might appear as a large and questionable flaw. The practice in the case of a marginal or questionable anomaly is to set the length of pipe aside and closely examine it with a hand held ultrasonic inspection device and/or by means of magnetic particle inspection. This, of course, requires additional handling of the questionable length of pipe and consumes valuable operator time.

It therefore is a primary object of this invention to provide a nondestructive magnetic inspection system that produces additional information that defines more certainly the type, orientation, and severity of an anomaly in an object being nondestructively tested. Although the discussion will deal with a specific type of inspection technique, i.e., magnetic flux leakage, it will be apparent to those skilled in the art that at least some of the evaluation and display principles described herein are applicable to other types of inspection techniques.

SUMMARY OF THE INVENTION

In this invention, significantly new and improved inspection results are achieved by inspecting an incremental region of a pipe wall, for example, with a first steady, or unidirectional, magnetic field component and a respective magnetic field detector device, and then inspecting the incremental regions with a second steady magnetic field component that is perpendicular to the first component and a second respective magnetic field detector. In practice, these two signals are obtained at a single inspection position by a single relatively rotating apparatus. Each incremental region of the pipe wall is inspected in this manner. The two inspection signals thus obtained from each incremental region are added together. This procedure substantially assures that the two magnetic fields will "see" all anomalies in the pipe wall.

Means are provided for providing an address for each incremental region that is inspected, and the added inspection signals emanating from each incremental region are stored at their corresponding address. The stored, added, inspection signals then are converted by means of a color code table to respective color signals that produce TV color signals that are indicative of the magnitudes of the stored signals, i.e., of the severity of the detected anomalies. The color signals are displayed on a color TV monitor in a manner to represent the locations of the anomalies on the pipe wall. The color TV presentation simulates the movement of a pipe, forward or backward, through the inspection apparatus.

BRIEF DESCRIPTION OF DRAWINGS

FIGS. 1-3 illustrate in simplified form means for establishing the desired magnetic field components in a pipe wall in accordance with the teachings of this invention;

FIGS. 4-6 illustrate in further detail the means that are illustrated in FIGS. 1-3;

DESCRIPTION OF PREFERRED EMBODIMENT

Figure 6:
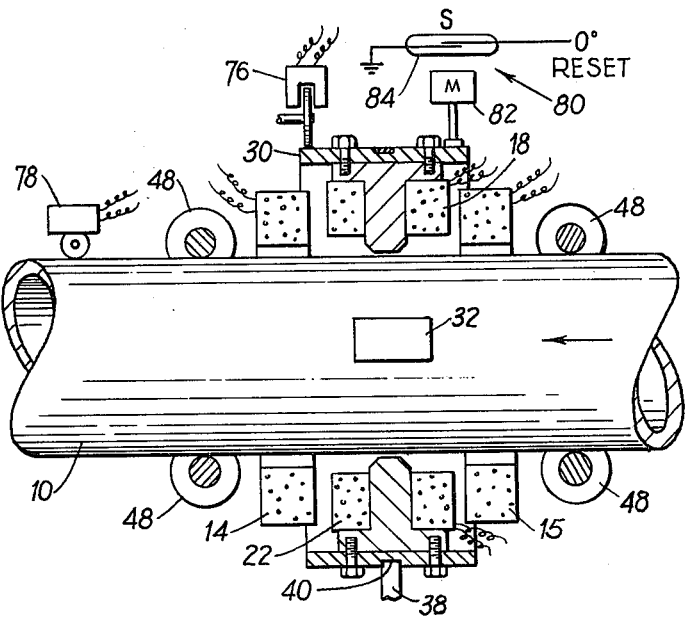

The first one of the important features of this invention will be described by referring to FIG. 1-6 which will be used in explaining how I am able to produce flux leakage from long, narrow cracks irrespective of their angular orientation in the pipe wall. As illustrated in FIG. 1, a length of steel pipe 10 has four long, narrow cracks a through d aligned on its wall. For discussion purposes, considering the projection of each of those cracks onto the longitudinal axis of the pipe, it may be said that crack a is oriented 45° counterclockwise to the axis, crack b is oriented perpendicularly to the axis; crack c is oriented 45° clockwise to the axis, and; crack d is parallel to the axis.

Wire coil electromagnets 14 and 15 are disposed circumferentially around pipe 10 and are energized by d.c. electrical sources 16 and 16′. Magnets 14 and 15 cooperate to establish a longitudinally directed steady, or unidirectional, magnetic field uniformly throughout the entire circumference of the pipe wall. At a given incremental region x in the pipe wall this longitudinal magnetic field may be represented by the longitudinal magnetic field vector $H_L$. As explained above, and assuming all cracks are the same severity, the perpendicularly extending crack b will produce an optimum fringing of the magnetic field $H_L$. The 45° cracks a and c each will produce an external fringing field of approximately half the magnitude of that produced by crack b. The parallel crack d will produce a minimal fringing.

Considering next the electromagnets 18 and 22 each energized by a respective d.c. electrical source 20 and 24, it is seen that the top pole piece is a north magnetic pole and the bottom pole piece is a south magnetic pole. As illustrated in FIG. 2, the transverse magnetic field source comprised of electromagnets 18 and 22 establishes a steady, or unidirectional, flux field that flows transversely across the pipe 10 in equal fields in the opposite sides of the pipe wall. At a given incremental region x in the pipe wall a transverse field component may be represented by the magnetic field vector $H_{T1}$. The transverse magnetic field component $H_{T1}$ will produce an optimum fringing field at crack d, approximately half that fringing field at cracks a and c (statistical results based on tests), and little or no fringing at crack b.

From the above discussion it is seen that the longitudinal field component $H_L$ and the transverse field component $H_{T1}$ will each fail to produce acceptable flux leakage from at least one of the cracks a-d.

The vector addition of these two orthogonal, simultaneously occurring components $H_L$ and $H_{T1}$ (which are assumed to be of equal magnitudes) produce a resultant steady resultant flux field $H_{R1}$ whose projection is 45 degrees clockwise to the longitudinal axis of the pipe. Resultant field $H_{R1}$ will produce minimal flux leakage field at crack c since they are parallel, will produce maximum flux leakage at crack a which is perpendicular, and approximately half said maximum leakage at cracks b and d both of which are oriented at 45° to the resultant field $H_{R1}$.

When the transverse magnetic field source comprised of electromagnets 18 and 22 is rotated so that the south magnetic pole piece is on top of the pipe and the north magnetic pole piece is below the pipe, as illustrated in FIG. 3, the direction of the transverse magnetic field vector $H_{T2}$ will be reversed by 180°. Transverse magnetic vector $H_{T2}$ will combine with longitudinal magnetic vector $H_L$ and the projection of the resultant steady resultant magnetic field vector $H_{R2}$ will be 45° counterclockwise to the longitudinal axis of the pipe, again assuming that component fields $H_L$ and $H_{T2}$ are equal in magnitude. This resultant field $H_{R2}$ will produce a maximum fringing field at the perpendicular crack C, approximately half that maximum field will be produced at cracks b and d, and minimal fringing field at parallel crack a.

From the above discussion it is seen that by rotating through 180° the transverse magnetic field source comprised of electromagnets 18 and 22 the variously oriented cracks a–d will produce the following percentages of optimum flux leakage, again assuming that all cracks are identical except for angular orientation, and that the two resultant fields $H_{R1}$ and $H_{R2}$ are equal in magnitude and are perpendicular to each other at opposite 45 degree inclination to the pipe axis.

| Crack | $H_{R1}$ | $H_{R2}$ | $H_{R1} + H_{R2}$ |
|---|---|---|---|
| a | 100% | 0% | 100% |
| b | 50 | 50 | 100 |
| c | 0 | 100 | 100 |
| d | 50 | 50 | 100 |

The magnetic field vector relationships illustrated in FIGS. 1 and 3 will exist throughout a major cross sectional portion of the pipe wall, as may be seen by reference to FIG. 2.

Flux leakage responsive detectors that pass over the cracks a–d when subjected to the respective resultant fields $H_{R1}$ and $H_{R2}$ will produce electrical voltages that correspond in relative magnitudes to the values set forth above. It can be seen that if the voltage responses of detectors that sense the flux leakage corresponding to the resultant fields $H_{R1}$ and $H_{R2}$ at the respective cracks can be added, the total response for each crack would be 100 percent of the optimum response, regardless of the angular orientation of the crack.

The construction and arrangement of the apparatus for producing the resultant magnetic flux field $H_{R1}$ and $H_{R2}$ and the detector means for detecting the flux leakage fields at the pipe wall anomalies (the cracks a–d of the above description being an example of but one type of anomaly), are illustrated in simplified form in FIGS. 4–8. A circular steel or iron yoke 30 that is a good magnetic flux conductor is rotatably and symmetrically supported (by means not illustrated) about pipe 10. Electromagnets 18 and 22 are physically attached to yoke 30 at locations 180 degrees apart and are in intimate magnetic circuit contact therewith. Electromagnets 18 and 22 produce the transverse field component $H_T$ of FIGS. 1 and 3. As seen in FIG. 6, two fixed and nonrotatable circular wire coil electromagnets 14 and 15 are disposed about pipe 10 on opposite sides of the electromagnets 18 and 22. Coils 14 and 15 are energized so that they produce magnetic fields in the same direction, i.e., aiding fields, in the wall of pipe 10. These aiding fields constitute the longitudinal field component $H_L$ of FIGS. 1 and 3.

Secured to rotatable steel yoke 30 at opposite locations between transverse field electromagnets 18 and 22 are two search shoes 32 and 34 that house the flux leakage field detectors. The detectors are closely adjacent the inside surface of the shoes so as to be as close as possible to the pipe surface as the shoes rotate about the pipe surface. It will be seen that shoes 32 and 34 are located on regions of the pipe where both the transverse field $H_T$ and the longitudinal field $H_L$ will be present with the relationships illustrated in FIGS. 1 and 3.

A drive belt or chain 38 is received in a circumferential slot 40 in steel yoke 30 and passes around sheave 42 on motor 44. The motor may be electrically or hydraulically actuated. As the motor rotates, belt 38 causes the rotatably supported yoke 30 to continuously rotate about the nonrotating pipe 10 so that a given incremental region within the magnetic fields first will see a resultant magnetic flux field $H_{R1}$ that is in a first direction through the region and 180° of rotation later the resultant magnetic flux field $H_{R2}$ will pass through the given incremental region in a direction that is perpendicular to the first direction, again assuming that the longitudinal and transverse components $H_L$ and $H_T$ are of equal magnitudes. This assumption will be carried throughout the remainder of the discussion unless expressly stated otherwise. It will be appreciated that in practice the components $H_{R1}$ and $H_{R2}$ do not have to be oriented exactly 90° to each other, although that relationship is presently preferred. Any substantial transverse relationship will produce the above-discussed result, although the combined result of $H_{R1}$ and $H_{R2}$ may not result in 100% of the optimum flux leakage fringing.

Pipe 10 is centrally supported within yoke 10 by rolls 48 that permit the pipe to advance linearly substantially without rotation. Conventional means such as drive rolls (not illustrated) may be used to advance pipe 10. It is seen from FIGS. 1 and 3 that relative rotation is required between pipe 10 and the transverse magnetic field means comprised of electromagnets 18 and 22. Of course, pipe 10 could be rotated relative to stationary yoke 30, but for practical reasons, the arrangement illustrated in FIG. 5 presently is preferred. The rates of longitudinal travel and rotational travel are chosen so that the magnetic fields will immerse all contiguous incremental regions of the pipe, i.e., 100% coverage.

The illustrations of FIG. 4–6 are simplified to facilitate the description and in order not to complicate the drawings and obscure the present invention. U.S. Pat. No. 3,582,771 issued to E. A. Placke on June 1, 1971 shows and describes rotating transverse magnetic field apparatus of the type illustrated in FIGS. 4–6. Reference is hereby made to that patent for specific details of the structure. Modification of that structure to include the stationary circular wire coils 14 and 15, FIG. 6, will be obvious to one skilled in the art. It is understood that in that patent it was not contemplated that each search shoe would cover 100% of the pipe surface.

The magnetic flux detector means within search shoes 32 and 34 may be any of a number of suitable types such as Hall effect probes or generators, magnetodiodes, or wire coils, for example. I presently prefer to use the Hall effect devices, and the following discussion will be based on the use of those devices. A suitable device is the FH-300 series Hall generators produced by F. W. Bell Inc., Columbus, Ohio, and described in its specification sheet number 70050. The devices are miniature solid state magnetic field sensing devices, each having four electrical connections. Two conductors carry the control current and two others supply the Hall output voltage. The Hall output voltage is directly proportional to the product of the control current and the magnetic field component that is normal to the Hall active area. The physical dimensions of a single device are 0.125"×0.100", and 0.020" thick.

As used in the present invention, the active area of the Hall device must be normal to the resultant magnetic field $H_R$. The active area is parallel to the 0.100"×0.125" surface of the device. In the present invention the resultant magnetic field $H_R$ is at an angle of 45 degrees to the longitudinal axis of the pipe. Consequently, the Hall devices must be oriented perpendicularly to that direction. As seen in FIGS. 4 and 5, two search shoes 32 and 34 are attached to rotating yoke 30.

Figure 7:
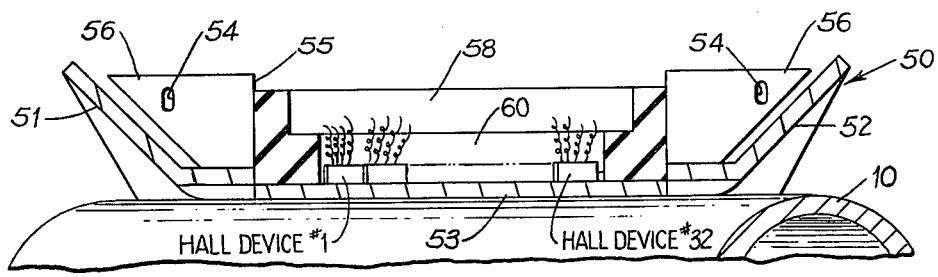
FIGS. 7 and 8 are simplified illustrations of a search shoe that may be used in the practice of this invention.
Figure 8:
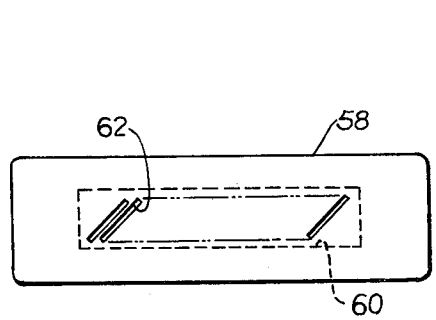

The long dimension of each shoe is parallel to the pipe longitudinal axis. FIGS. 7 and 8 illustrate in simplified form the arrangement of the Hall devices within search shoes 32 and 34.

FIG. 7 is a simplified illustration of a search shoe that has a metallic frame 50 of a nonmagnetic material such as stainless steel. The shoe has upwardly inclined leading and trailing edges 51 and 52 and its bottom surface 53 is curved to conform to the outer surface of pipe 10. The shoe is attached to a suitable support mechanism (not illustrated) by means of fasteners that extend through the elongated mounting holes 54 on side brackets 56. Cavity 55 is located in the central region of the shoe between the side walls that form the side brackets 56. A Hall probe mounting means 58 is disposed within cavity 55 and may be securely held therein by means of suitable fasteners. A recessed portion 60 within mounting means 58 extends through the mid-region of mounting means 58 and is adapted to receive the 32 Hall effect devices that are mounted within the shoe. FIG. 8 is a bottom view of mounting means 58 and shows 32 saw cuts into the bottom surface of the mounting means. These saw cuts are at an angle of 45° to the longitudinal axis of the mounting means and extend into the body of the mounting means a distance of approximately 0.06 inch. The Hall effect devices are mounted within these saw cuts in a linear array that is parallel to the longitudinal axis of the mounting means. In practice, the axial length of the recessed portion 60 in the bottom of mounting means 58 is approximately 3.2 inches. Therefore, the 32 Hall devices will be longitudinally spaced from each other by approximately one-tenth inch. As will be explained below, the output voltages of the Hall effect devices are sequentially sampled and ultimately displayed for visual presentation. In effect, each search shoe is "looking at" a 3.2 inch line that is parallel to the pipe axis and is taking a "look" each one-tenth inch along this line.

FIG. 8 illustrates the saw cuts 62 oriented at a 45° angle. It was stated above that the active face of a Hall effect device must be perpendicular to the direction of the steady resultant magnetic field $H_R$. Therefore, if the saw cuts 62 are oriented 45° in the clockwise direction in one shoe, they will have to be oriented counterclockwise in the other shoe in order to preserve the required orientation between the resultant magnetic field $H_R$ and the active face of the Hall effect device on the opposite side of the pipe.

A feature of this invention is that each search shoe of a pair of search shoes inspects the same surface area of a pipe as the other shoe of that pair as they rotate about the pipe.

This is achieved by rotating the magnetic yoke 30, FIG. 5, at a relatively high rotational speed so that regardless of how fast pipe 10 will move longitudinally, as a practical matter, in apparatus having just one pair of search shoes each helical convolution travelled by a search shoe will overlap the last helical convolution made by that same search shoe. Futhermore, there is substantial overlap of the coverage of shoe 32 (shoe 1) by shoe 34 (shoe 2) during one complete revolution of rotating yoke 30. As an example, in one embodiment of the invention the flux leakage field sampled by Hall effect devices 1-16 (leading half of Hall probes) in shoe 1 were sampled by Hall effect devices 17-32 (trailing half of Hall probes) in shoe 2 one-half revolution later, and vice versa.

Search shoes 32 and 34 are axially aligned on the pipe surface, and because of their high rate of rotation relative to the longitudinal motion of pipe 10, the substantial overlap of the coverage of shoe 1 by shoe 2 still is achievable. This means that changes in the rotational speed of yoke 30 and/or in the linear travel of pipe 10 are not required for different pipe sizes. A further advantage of having search shoes 32 and 34 axially aligned is that the transverse magnetic field $H_T$ may be more narrow than if shoe 34 was axially behind shoe 32 and followed it around the pipe on the same helical path. This means that the electromagnet means 18, 22 required to produce a desired strength of transverse magnetic field $H_T$ need not be as large and need not consume as much power.

From the above discussion it is seen that regardless of the angular orientation of the elongated cracks a-d of FIGS. 1 and 3 each one will be detected by the flux leakage detector means in one or both of the search shoes 32 and 34. Being able to detect the existence of an anomaly at any angular orientation in the pipe wall is indeed necessary in order to provide a competent evaluation of the condition of the pipe. However, without more, the operator may have difficulty in determining the exact nature and severity of the anomaly, or he may be completely unable to make such determination without extensive further examination. The above described technique of alternately passing both orthogonally directed resultant flux fields $H_{R1}$ and $H_{R2}$ through each incremental region of pipe wall and detecting the respective flux leakage fields at each incremental region lends itself well to new techniques for deriving considerably more information from the detected flux leakage signals than was formerly possible. As will now be explained, I am able to provide a visual indication of the anomaly that conveys added information as to the type of anomaly and its severity. I am able in most instances to present an outline of the anomaly on the face of a cathode ray tube (CRT), and by means of color coding I am able to indicate the degree of severity of the anomaly, or the degrees of severity of various different parts of a large, nonuniform anomaly.

An overall broad and somewhat general description of the inspection signal processing and display portion of the present invention will be given by referring to the simplified block diagram of FIG. 9. A more detailed description of the specific structure and operation of the blocks within the system will be given later. The 32 Hall probes that comprise the flux leakage detectors of shoe 1 and the 32 detectors of shoe 2 are individually coupled through respective preamplifiers 70 and suitable noise filtering means (not illustrated) to a 64 channel multiplexer (MUX) 72. MUX 72 is a conventional analog signal switching device having a respective switching means for each input line. The switches are individually actuated by a coded address signal coupled in on address line 74. A succession of coded address signals causes the 64 switches of MUX 74 to be sequentially closed and then opened at a rate of 0.5 MHz so that the input inspection signals from the 64 detectors are sequentially sampled and coupled out on the single output line 73.

Figure 9:
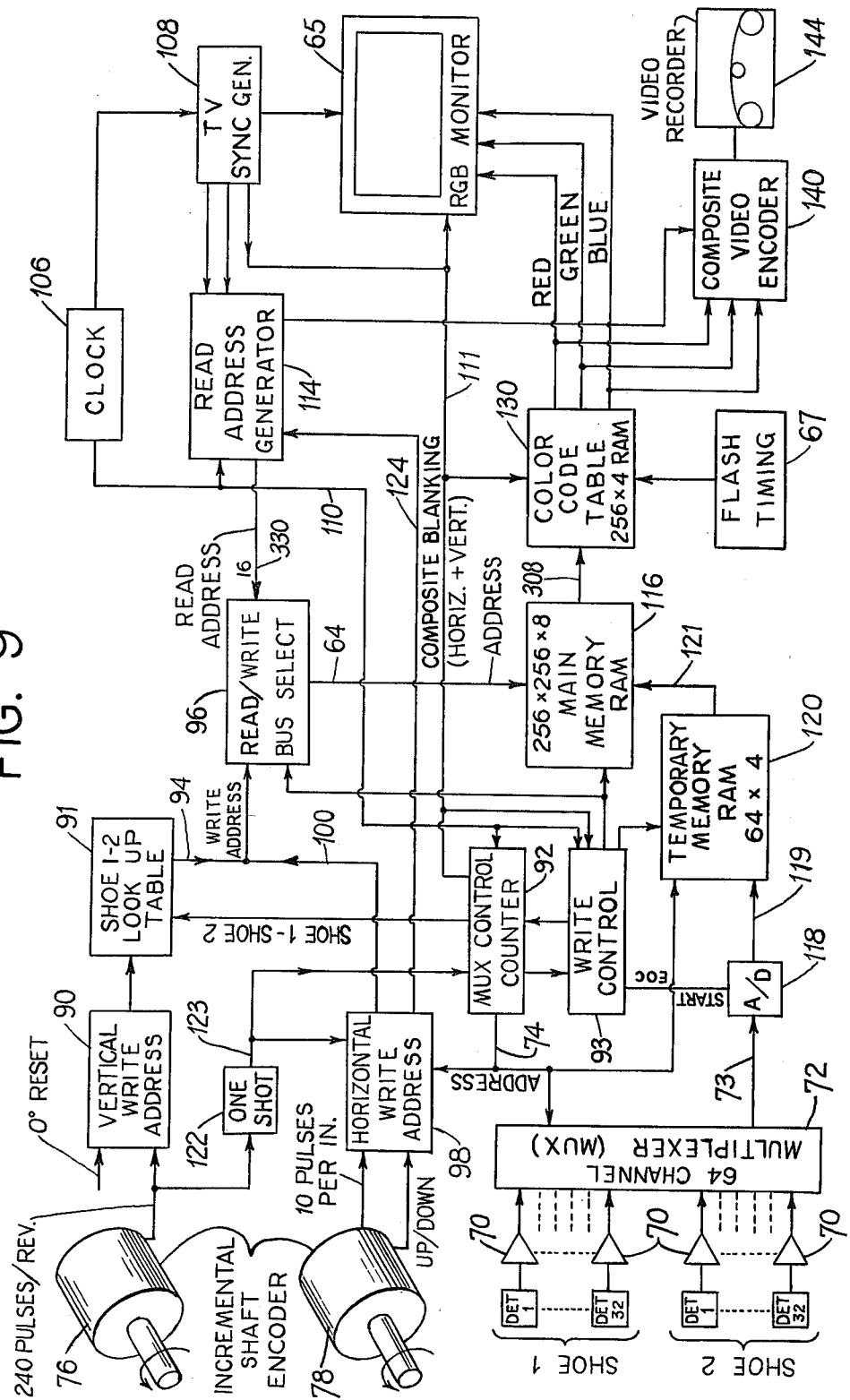
FIG. 9 is a simplified block diagram of an inspection system constructed in accordance with the teachings of this invention.

It is absolutely necessary that the system of FIG. 9 keep track of the exact incremental regions on pipe 10 where the inspection signals are coming from. This is accomplished by means of the incremental shaft encoders 76 and 78 illustrated in the upper left corner of FIG. 9, and the zero degree rotation detector means 80 illustrated at the upper right of FIG. 6. The latter device may be comprised of a small permanent magnet 82 that is secured to rotating yoke 30. A stationary magnet detector such as the illustrated reed switch, or a wire coil, or a Hall device, is fixed relative to rotating yoke 30 and produces a pulse signal each time rotating magnet 82 passes the fixed detector 84. This output pulse from detector 84 is the 0° reference pulse, and in cooperation with the succession of output pulses from circumferential encoder 76, FIG. 9, provides a means for establishing angular reference data to correlate with the angular locations of the Hall effect devices in search shoes 32 and 34 as they scan the pipe surface.

The magnetic yoke 30 of FIGS. 4-6 may be rotated at a rate of 320 revolutions per minute, as an example, and circumferential shaft encoder 76 will produce a succession of pulses at a rate of 240 pulses per revolution, i.e., 1280 pulses per second, wherein each pulse represents a 1.5° angular advancement of yoke 30 and thus of search shoes 32 and 34. These pulses are coupled as one input to vertical write address circuitry 90 that includes an 8 bit up counter that counts the angular pulses. Each time permanent magnet 82 of FIG. 6 passes reed switch 84 a 0° reset pulse is coupled to the vertical write address circuitry to reset the counter. The counter then commences to count up again until another rotation of yoke 30 is completed, at which time another 0° reset pulse is generated and the counter again is reset.

The system also must keep track of which search shoe the sampled signals are coming from. For this purpose, a coded signal (a zero or a one bit signal) is coupled from MUX control counter 92 to shoe 1-2 look up table 91 to code the address from vertical write address circuit 90 as to whether the signal being sampled is coming from a Hall probe in shoe 1 or shoe 2. The coded circumferential location of a simultaneously sampled Hall probe then is coupled to output line 94.

Because the second search shoe 34 trails the first search shoe 32 by 180° (a count of 120 pulses from circumferential incremental encoder 76) the address that is generated in vertical write address circuitry 90 is incremented by a count of 120 by shoe 1-2 look up table 91 for all addresses corresponding to sampled signals from search shoe 2. This relationship is shown in the following table.

| Rotation/ Count | 0°- 1.5° | 1.5°-180° | 180°-181.5° | 181.5°-358.5° | 358.5°-0° |
|---|---|---|---|---|---|
| Shoe #1 | 1 | 2-120 | 121 | 122-239 | 240 |
| Shoe #2 | 121 | 122-240 | 1 | 2-119 | 120 |

The horizontal location along pipe 10 where an inspection signal is coming from is established in coded form by means of horizontal shaft encoder 78 that produces one output pulse for each one-tenth inch of linear travel of pipe 10. At a rate of linear travel of 80 feet per minute, as an example, encoder 78 will produce pulses at a rate of 160 pulses per second. Encoder 78 also produces a coded signal indicating whether pipe 10 is moving in the forward or the reverse direction. These two output signals are coupled to respective inputs of horizontal write address circuitry 98. This circuitry includes an up/down counter that counts up to successive overflows and resets as pipe 10 travels in the forward direction, and counts down as the pipe travels in the reverse direction. Counting pulses from linear encoder 78 will give a linear location of the first one of the Hall elements in each of the search shoes on pipe 10, but it will not give the exact location of each of the remaining Hall probes within a shoe that is being sampled by MUX 72 at a particular time. Accordingly, a second succession of sequentially occurring address signals at a rate of 2.04 MHz that appear on line 74 from MUX control counter 92 is coupled to horizontal write address circuitry 98 and is added to a respective address that is accumulated in the up/down counter in response to the output of linear encoder 78. The 8 bit circumferential write address on line 94 and the 8 bit horizontal write address on line 100 are combined into a 16 bit word and are coupled to read/write bus select circuit 96.

Incremental shaft encoders suitable for the circumferential and linear encoders 76 and 78 of FIG. 9 are well known and commercially available. One suitable type encoder is the Instrument Grade Type L25 Incremental Optical Encoder, obtainable from BEI Electronics, Inc., Goleta, Calif.

From the above discussion it is evident that each Hall probe is inspecting an incremental region of the pipe that is one-tenth inch long and 1.5° in circumferential extent. Because of the relative rate of rotation and the 100% inspection coverage by both magnetic fields and the search shoes, all contiguous incremental regions of a pipe are inspected.

Sampling of the 64 Hall devices in the two search shoes and the forming and writing of the addresses corresponding to the circumferential and longitudinal positions of the sampled Hall devices are under control of timing signals emanating from system clock 106 and TV camera sync generator circuit 108. This latter circuit is a commercially available LSI chip type MM5320 that supplies the basic sync functional signals to a conventional TV color camera. In particular, a 2.04 MHz clock signal is coupled from clock 106 on line 110 to MUX control counter 92 and to write control circuit 93. Additionally, a composite blanking signal (horizontal and vertical blanking signals) are coupled from TV sync generator 108 on line 111 to MUX control circuit 92 and write control circuit 93.

Having successively sampled each of the 64 Hall probe detectors, and obtained respective inspection signals, and having generated respective circumferential and longitudinal addresses for each of the sampled detectors, that information now must be placed in the main memory RAM 116. This operation is under primary control of MUX control counter 92 and write control circuit 93. The 64 Hall detectors are sampled in succession at a rate of 0.5 MHz. Sampled signals from multiplexer 72 are coupled at that same rate to analog to digital (A/D) converter 118 where they are simultaneously converted to corresponding digital signals. These digital signals are coupled to temporary memory RAM 120 at the 0.5 MHz rate. The MUX address signal on line 74 addresses the inspection signals in temporary memory RAM 120. This sampling of Hall effect probes, the conversion of the sampled signals into digital form, and their storage into temporary memory RAM 120, is initiated by a 1.5° output pulse from circumferential incremental shaft encoder 76. Each 1.5° pulse triggers one shot 122 whose output comprises a reset pulse that resets MUX control counter 92. The MUX counter 92 then commenses to produce the 64 successively occurring addresses that are coupled to multiplexer 72. This is the first of two such successions of addresses that MUX counter 92 produces.

The digitally coded inspection signals in temporary memory RAM 120 can be read into main memory RAM 116 only during the occurrence of a horizontal or vertical blanking signal from TV sync generator 108. The blanking signals are coupled over lead 111 to MUX control counter 92 and write control circuit 93. During the occurrence of one of these blanking signals, and after the last one of the first succession of 64 MUX address signals at the sampling rate of 0.5 MHz, MUX control counter 92 will provide a second succession of 64 MUX address signals at a rate of 2.04 MHz to temporary memory RAM 120 and to horizontal write address circuit 98. The contents of temporary memory 120 will be read out at the rate of 2.04 MHz and transferred to the main memory RAM 116. Simultaneously with the transfer of data from the temporary memory to the main memory, a write signal will be coupled from write control circuit 93 to read/write bus selected circuit 96 to transfer the then occurring write address from horizontal write address circuit 98 to main memory RAM 116 so that data may be stored at a rate of 2.04 MHz at an address corresponding to the position on the pipe where the signal originated.

In practice, the write addresses coupled through read/write bus select switch 96 will not change during the sampling and storing process of data from a specific Hall device. Also because of timing considerations, only 1/16th of temporary memory RAM 120 will be read during the occurrence of a horizontal retrace blanking signal. Consequently, at least 4 horizontal retrace blanking signals must occur in order to transfer the entire contents of temporary memory RAM 120 to main memory RAM 116. On the other hand, the duration of a vertical retrace blanking signal is long enough so that the entire contents of temporary memory RAM 120 may be transferred to the main memory RAM 116 during the occurrence of one vertical blanking signal. In any event, the contents of temporary memory RAM 120 are completely transferred to main memory 116 before the Hall effect probes are again sampled.

An alternative mode of operation for sampling the Hall probes in shoes 1 and 2 and for transferring the sampled inspection signals to main memory RAM 116 is as follows. MUX control circuit 92 may contain two counters. One counter, the sampling counter, controls the sequential sampling of the Hall probes. The second counter, the transfer counter, controls the transfer of digital data from temporary memory RAM 120 to main memory RAM 116. The sampling counter is interrupted by each composite blanking signal on line 111 and then resumes its sampling after the blanking signal terminates. The transfer counter operates during the occurrence of each blanking signal to transfer data from temporary memory to main memory. Each counter resumes its counting after its interrupt period has terminated. Comparator means are provided to stop the transfer counter when its count equals the count in the sampling counter. This latter condition indicates that the content of the temporary memory RAM 120 have been completely transferred. The sampling counter is permitted to count anytime the transfer counter is not counting. This alternative sample and transfer mode usually is somewhat faster in operation than the method described above.

Main memory RAM 116 is a 256×256×8 memory wherein each 8 bit word that is stored is made up of the two 4 bit nibbles that correspond to the inspection signals produced by shoe 1 and shoe 2 detectors when, respectively, the first steady resultant magnetic field component $H_{R1}$ and then the perpendicularly or orthogonally oriented steady magnetic field component $H_{R2}$ pass through the exact same incremental region on pipe 10. It was mentioned above that the shoe 1-2 look-up table 91 added a count of 120 (180°) to the output of a vertical (circumferential) write address counter 90 each time multiplexer 72 sampled a Hall probe in shoe 2. It also was mentioned that the horizontal address was comprised of the addition of the linear position of a shoe and the exact location of the Hall probe that was being sampled in that shoe at a given time. Consequently, the exact location of the incremental region where each inspection signal was detected is kept track of by the address circuits. By automatically accounting for the 180° spacial separation between the shoes in forming the vertical address codes, main memory RAM 116 automatically will store side-by-side (8 bit word) the coded inspection signals detected by Hall probes in shoe 1 and shoe 2 at the same incremental location on pipe 10.

Figure 10:
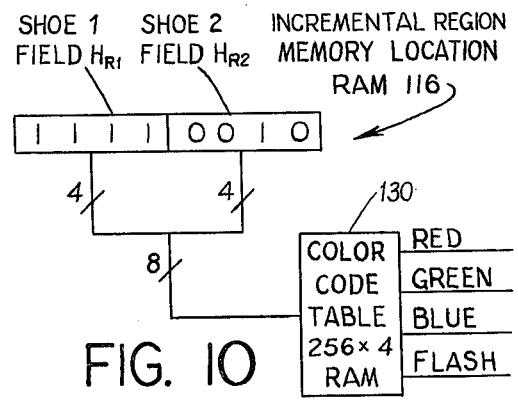
FIG. 10 is a pictoral representation of a storage location in a memory device in the system of FIG. 9.

FIG. 10 represents an 8 bit storage location in main memory RAM 116 and illustrates the matter just discussed. The 4 bit nibble in the left side of the memory location is the binary coded signal representing the magnitude of the flux leakage signal that was detected when the first resultant magnetic field component $H_{R1}$ was incident on the particular incremental region and was detected by shoe 1. The 4 bit binary coded signal in the right side of the memory location represents the magnitude of the flux leakage signal that was detected when the perpendicularly oriented resultant magnetic field component $H_{R2}$ was incident on that particular incremental region of the pipe and was detected by shoe 2.

It may be understood from the above discussion that significantly improved inspection of the pipe wall is achieved by inspecting each incremental region of the pipe with a steady magnetic field that is directed in a first direction, then inspecting each incremental region with a second steady magnetic field that is in a transverse, preferably perpendicular, direction, and then combining for each incremental region the two inspection signals obtained. The means for providing the perpendicularly oriented fields permits the above operation to be accomplished at a single inspection position with relatively simple apparatus having circumferential motion relative to the pipe.

In accordance with a further feature of this invention it is desired to display the magnitude of the combined inspection signals corresponding to each incremental region on a cathode ray tube with a color code wherein different colors represent different severities of detected anomalies. The manner in which the color coding is correlated to the magnitude of the detected anomalies is represented in the following Color Code Table.

COLOR CODE TABLE

| Shoe 1 | Shoe 2 | Video Gun Drive Code | | |
|---|---|---|---|---|
| | | Flash | Red | Green | Blue |
| 00 | | | | | |
| 01 | 10 | | | | |

COLOR CODE TABLE -continued

```
                              02  11  20
                           03  12  21  30                           0  0  0  1  Blue
                        04  13  22  31  40
                     05  14  23  32  41  50
                  06  15  24  33  42  51  60                        0  0  1  0  Green
               07  16  25  34  43  52  61  70
            08  17  26  35  44  53  62  71  80                      0  0  1  1  Cyan
         09  18  27  36  45  54  63  72  81  90
      0A  19  28  37  46  55  64  73  82  91  A0
   0B  1A  29  38  47  56  65  74  83  92  A1  B0                   0  1  1  0  Yellow
0C  1B  2A  39  48  57  66  75  84  93  A2  B1  C0
0D  1C  2B  3A  49  58  67  76  85  94  A3  B2  C1  D0
0E  1D  2C  3B  4A  59  68  77  86  95  A4  B3  C2  D1  E0          0  1  0  1  Magenta
0F  1E  2D  3C  4B  5A  69  78  87  96  A5  B4  C3  D2  E1  F0
1F  2E  3D  4C  5B  6A  79  88  97  A6  B5  C4  D3  E2  F1
2F  3E  4D  5C  6B  7A  89  98  A7  B6  C5  D4  E3  F2              1  1  0  0  Red
3F  4E  5D  6C  7B  8A  99  A8  B7  E6  D5  C4  F3
4F  5E  6D  7C  8B  9A  A9  B8  C7  D6  E5  F4
5F  6E  7D  8C  9B  AA  B9  C8  D7  E6  F5
6F  7E  8D  9C  AB  BA  C9  D8  E7  F6
7F  8E  9D  AC  BB  CA  D9  E8  F7
8F  9E  AD  BC  CB  DA  E9  F8
9F  AE  BD  CC  DD  EA  F9
AF  BE  CD  DC  EB  FA
BF  CE  DD  EC  FB
CF  DE  ED  FC
DF  EE  FD
EF  FE
FF
```

Because the magnitudes of the inspection signals detected by the respective shoes are represented by 4 bit binary nibbles, the maximum magnitude that can be represented by a nibble is decimal 15. The hexadecimal representation of O through F is used in the Color Code Table to represent the magnitudes 0–15 in decimal notation. The Color Code Table is comprised of a plurality of 2 digit pairs of numbers and/or letters arranged in an overall diamond-shape pattern. Looking at the very upper tip of the diamond-shape, the pair of digits is 00. The first 0 represents the magnitude of the inspection signal detected by shoe 1 when the first one of the magnetic fields $H_{R1}$ was at a given incremental region. The second 0 represents the magnitude of the inspection signal detected by shoe 2 when the perpendicularly oriented magnetic field $H_{R2}$ was present at the same given incremental region on the pipe. The pairs of numerals and/or letters therefore represent various combinations of magnitudes of signals detected at an incremental region by the two shoes. In using the Color Code Table, pairs of numbers and/or letters representing the magnitudes of detected inspection signals are added together to obtain their sum value. It will be noted that all pairs of numbers and/or letters along a horizontal line add up to the same total value. These summed values are the values that are to be color coded.

On the right margin of the Color Code Table are the colors to be displayed which correspond to the summed magnitudes of the coded inspection signals. For example, all summed pairs of digits whose total is 3 or less is represented by the blue color, thereby indicating the least severe anomalies. All summed pairs of digits whose total is between 4 and 6 will be coded by a green color. The pairs that total 7 and 8 will be represented by a cyan color, and so on through the Color Code Table. It is seen that all pairs having a summation of 15 through 30 (FF) will be represented by a red color, thereby indicating the most severe anomalies.

Also shown on the right of the Color Code Table are the video gun drive code signals that represent the output signals that appear on the output lines of the color code table RAM 130, FIGS. 9, 10. It is seen that the four bit gun drive code includes one bit labeled "Flash". A one in this bit position causes the red signal to continually flash on and off so as to alert the operator to possible severe anomalies.

Figure 11:
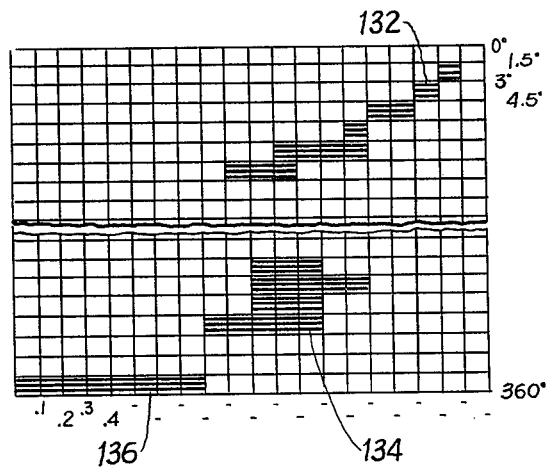
FIG. 11 and 12 are simplified illustrations of a TV presentation of a type produced in the system of FIG. 9.
Figure 12:
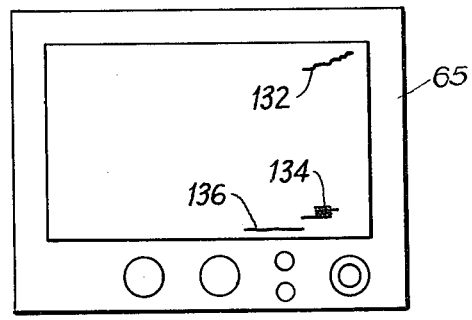

The color code signals occur in proper syncronization with the control signals for the color TV monitor 65 to present a color coded pictorial image of the inspected portion of a pipe wall. For example in FIG. 11, the vertical graduations on the scale represent the 1.5° circumferential increments around the circumference of a pipe and the horizontal graduations represent the one-tenth inch increments longitudinally along the pipe, said increments being produced by the circumferential and horizontal incremental shaft encoders 76 and 78 of FIG. 9. If it is assumed that the presentations indicated at 132, 134 and 136 are actual anomalies in the wall of the pipe, they will be represented on the face of the color TV monitor in a manner presented in FIG. 12, wherein the coloring within the outline of the respective anomalies will be coded in accordance with the magnitudes of inspection signals detected within the correspondingly located grid squares of FIG. 11. With the storage capabilities indicated above, the TV presentation actually can show 25.6 inches of a pipe.

As illustrated in FIG. 9, the syncronized color coded output signals from color code table RAM 130 also are coupled to a commercially available composite video encoder 140 which properly combines color signals and TV sync signals for recording on video recorder 144. The color coded inspection signal thus may be permanently stored for later examination and/or for detailed analysis at the inspection site.

In the embodiment of the invention described above, one pair of magnetic pole pieces comprised of electromagnets 18 and 22 was used to establish the transverse magnetic field component $H_T$. Similarly, one pair of search shoes 32 and 34 was used to scan the pipe surface. This arrangement is quite satisfactory for inspecting smaller diameter pipe. For the inspection of larger diameter pipe, however, the longer length of the magnetic path between two magnetic poles may require exceedingly large electromagnets 18 and 22. Additionally, because each shoe must cover 100% of the very large pipe surface, the rate of axial travel of the pipe may be somewhat limited, thus limiting the productivity of the apparatus.

These limitations of a two pole magnetic source for the transverse magnetic field component may be overcome by employing four, six, eight, or more even numbers of magnetic poles angularly spaced around yoke 30 and alternating in magnetic polarity. For example, in FIG. 13, four electromagnets 162, 164, 166 and 168 are equiangularly spaced about yoke 30 with their respective pole faces adjacent the outer surface of pipe 10. Electromagnets 162, 164 are, respectively, north and south magnetic poles, as are the respective electromagnets 166, 168. The first pair 162, 164 will establish a transverse magnetic field component that flows in the quadrant 172 of the pipe wall with the flux lines flowing from north pole 162 to south pole 164. A second transverse magnetic field component will be established in quadrant 174 of the pipe wall with its flux lines flowing from north pole 166 to south pole 164. These two transverse magnetic field components are in opposite directions with respect to each other so that when they each combine with the longitudinally directed steady magnetic field component $H_L$ that is established by wire coil electromagnets such as 14 and 15 of FIG. 6, first and second mutually perpendicular, or orthogonal, resultant magnetic field components will be established in the respective quadrants 172 and 174. With these perpendicularly directed fields in adjacent quadrants of the pipe wall, only 90° of relative rotation is required between the pole pieces 162, 164, 166 and the pipe to assure that first one resultant magnetic field component and then the perpendicularly directed component will successively be directed through any given incremental region of the pipe wall. As described in connection with FIGS. 1 and 3, these perpendicular resultant fields will assure that one or the other, or both, will "see" all of the elongated anomalies a-d that are illustrated in FIGS. 1 and 3.

The same considerations hold true for quadrants 176 and 178 of the pipe wall. A third transverse magnetic field component will be established between north magnetic pole 166 and south magnetic pole 168, and an oppositely directed fourth transverse magnetic field component will be established between north magnetic pole 162 and south magnetic pole 168. These third and fourth transverse magnetic field components each will combine with the longitudinally directed magnetic field component $H_L$ and will produce in the quadrants 176 and 178 of the pipe respective resultant magnetic field components that are perpendicular to each other. These third and fourth perpendicularly oriented resultant magnetic fields also will "see" all of the elongated anomalies a-d of FIGS. 1 and 3 after 90° relative rotation between the electromagnets and the pipe wall, as previously explained.

Figure 13:
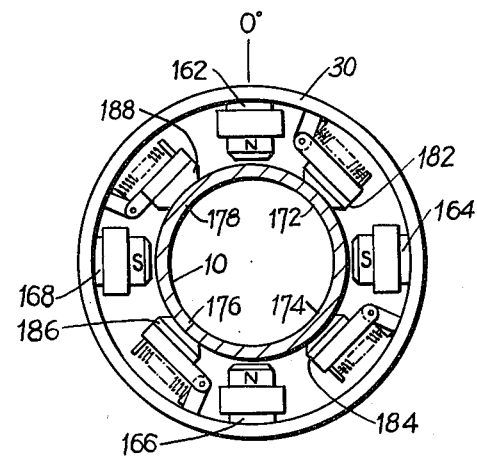
FIG. 13 is a simplified illustration of an alternative embodiment of multiple transverse magnetic field producing apparatus.

In view of the above considerations, each pair of shoes, wherein a pair is defined as two adjacent shoes in the embodiment of FIG. 13, needs to inspect only 50% of the pipe surface since the other pair can inspect the remaining 50%. It is to be understood that regardless of the number of pairs of shoes, the shoes in a pair inspect the same region of the pipe. In practice, the inspection coverages of the two pairs will be interlaced so that 100% coverage by the two pairs is assured. As one example, assume that pipe 10 is moving from right to left and that yoke 30 in FIG. 13 is rotating in the counterclockwise direction so that shoes 182, 184, 186, 188 successively pass the 0° reference position. Again assuming that each shoe has 32 axially aligned Hall probes as described in connection with FIGS. 7 and 8, the coverage by the respective shoes at the 0° position on pipe 10 will be as follows. Shoe 172 will inspect 32 incremental regions immediately under its 32 Hall probes. After 90° relative rotation Hall probes 1-16 of the second shoe 184 will inspect substantially the same incremental regions of the pipe as did Hall probes 17-32 of the first shoe 172, and Hall probes 17-32 of the second shoe will inspect the 16 incremental regions behind the 16 inspected by its Hall probes 1-16. After 90° further relative rotation Hall probes 1-16 of the third shoe 186 will inspect the same incremental regions of the pipe that were inspected by Hall probes 17-32 of the second shoe, and Hall probes 17-32 of the third shoe will inspect 16 incremental regions following those inspected by its first 16 Hall probes. Similarly, when the fourth shoe 188 reaches the 0° reference position its Hall probes 1-16 will inspect the same 16 incremental regions that were inspected by Hall probes 17-32 of the third shoe 186.

On the next revolution of the first shoe 182 to the 0° position its Hall probes 1-16 will inspect the same incremental regions that were inspected by Hall probes 17-32 of the fourth shoe 188. And so on, as the yoke 30 continues to rotate and pipe 10 continues to move axially.

During all of the above operations, circumferential and axial incremental encoders 76 and 78 of FIG. 9 continue to produce their incremental pulses that continually produce addresses that keep track of the positions of the four shoes and the incremental regions that are being inspected. Because four search shoes are employed, multiplexer 72, MUX control counter 92 and write control circuit 93 will be adapted to sample 32 Hall probes in each of the four shoes rather than the two shoes illustrated in FIG. 9. Further, MUX control counter 92 must keep track of which one of the four shoes is being sampled at a given time. Coded signals corresponding to the sampled shoe will be coupled to shoe look-up table 91 in order to appropriately encode the output of vertical write address circuit 90 to thereby designate the location of the shoe when it is being sampled.

Figure 14:
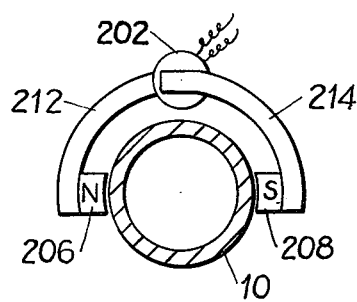
FIGS. 14 and 15 are simplified embodiments of a further alternative magnetic field producing apparatus.
Figure 15:
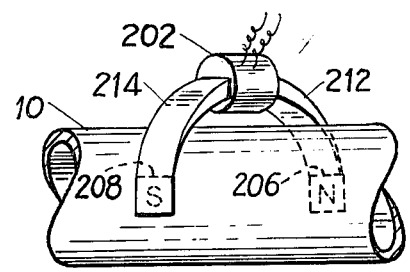

FIG. 6 illustrates one possible arrangement for producing resultant magnetic field components that are perpendicular to each other at a given incremental region, wherein the perpendicular relationship occurs after a predetermined relative rotation between the pipe and the transverse magnetic field source. Another possible arrangement for producing the perpendicularly oriented magnetic field components at an incremental region is illustrated in simplified form in FIGS. 14 and 15. In this arrangement an electromagnet 202 is magnetically coupled to respective pole pieces 206, 208 by means of a magnetic structure that is comprised of a central region 210 and respective legs 212 and 214 that are in contact with pole pieces 208 and 206. The pole pieces 206 and 208 are axially displaced with respect to each other and are angularly displaced about the surface of the pipe wall by an angle of 180° in the example illustrated. With the arrangement illustrated in FIG. 15 the magnetic flux field will enter the pipe wall from north magnetic pole 206 will divide and pass around both sides of the pipe to south magnetic pole 28 in paths whose projections are oblique to the axis of the pipe. When the magnetic structure is rotated 180° relative to the position illustrated in FIG. 15 the magnetic flux paths from north pole 206 through the pipe wall to south pole 208 will be transverse to the paths that existed prior to the rotation of the magnetic structure. The transverse direction of the crossing of the flux paths can be made to be a right angle by proper selection of dimension of the magnetic structure relative to the site of the pipe.

It will be understood that the source of a steady magnetic field, or fields, may be permanent magnets rather than electromagnets. Furthermore, the same principle discussed above could be applied to the nondestructive inspection of a buried pipeline by including the equipment in a pipeline pig that is propelled through the pipeline by the product being transported therethrough. In such case, multiple pairs of magnetic poles and shoes would be employed adjacent the pipeline wall. The inspection pig could be made to follow a helical or spiral path through the pipeline by means of canted rollers, wheels, etc. that engage the pipe wall. In such an apparatus the color television display means would not be employed. Rather, the inspection signals would be recorded on a suitable recording medium such as magnetic tape or disc carried by the inspection pig. Upon recovery of the pig from the pipeline the recording would be removed and used in conjunction with a suitable color display means to provide the type of visual display discussion above.

It also would be obvious to those skilled in the art that the multicolor, detailed video presentation of the inspection signals greatly improves the information available to the operator and provides inspection information not heretofore available. This type of presentation system is not limited to a magnetic flux leakage inspection system but may be used with other types of inspection systems such as ultrasonic eddycurrent, magnetometer xray, gamma ray, etc.

DETAILED CIRCUIT DESCRIPTION

The following is a more detailed description of the individual functional features of the system that is illustrated in simplified form in FIG. 9. FIGS. 16-21 correspond to the circuitry and components on respective printed circuit boards. For example, FIG. 16 corresponds to a printed circuit board A; FIG. 17 corresponds to a printed circuit board B; and so on through board M. In the drawings, some leads are identified only by numerals and some are identified by a letter and a numeral or numerals. The leads with only a numeral are to be understood to be associated with its respective printed circuit board and leads identified with a letter and numeral refer to the similarly numbered leads on the circuit board having that letter. For example, in the lower right corner of FIG. 16, board A, the leads 49, 50, 51 and 52 of board A also are designated as E-56, E-57, E-58 and E-59. Referring to printed circuit board E, FIG. 20, it is seen at the lower left that input leads A-49, A-50, A-51 and A-52 connect to leads 56, 57, 58 and 59 on board E. This type of lead and board designation will be used in the description of FIGS. 16-21.

VERTICAL WRITE ADDRESS

Figure 16:
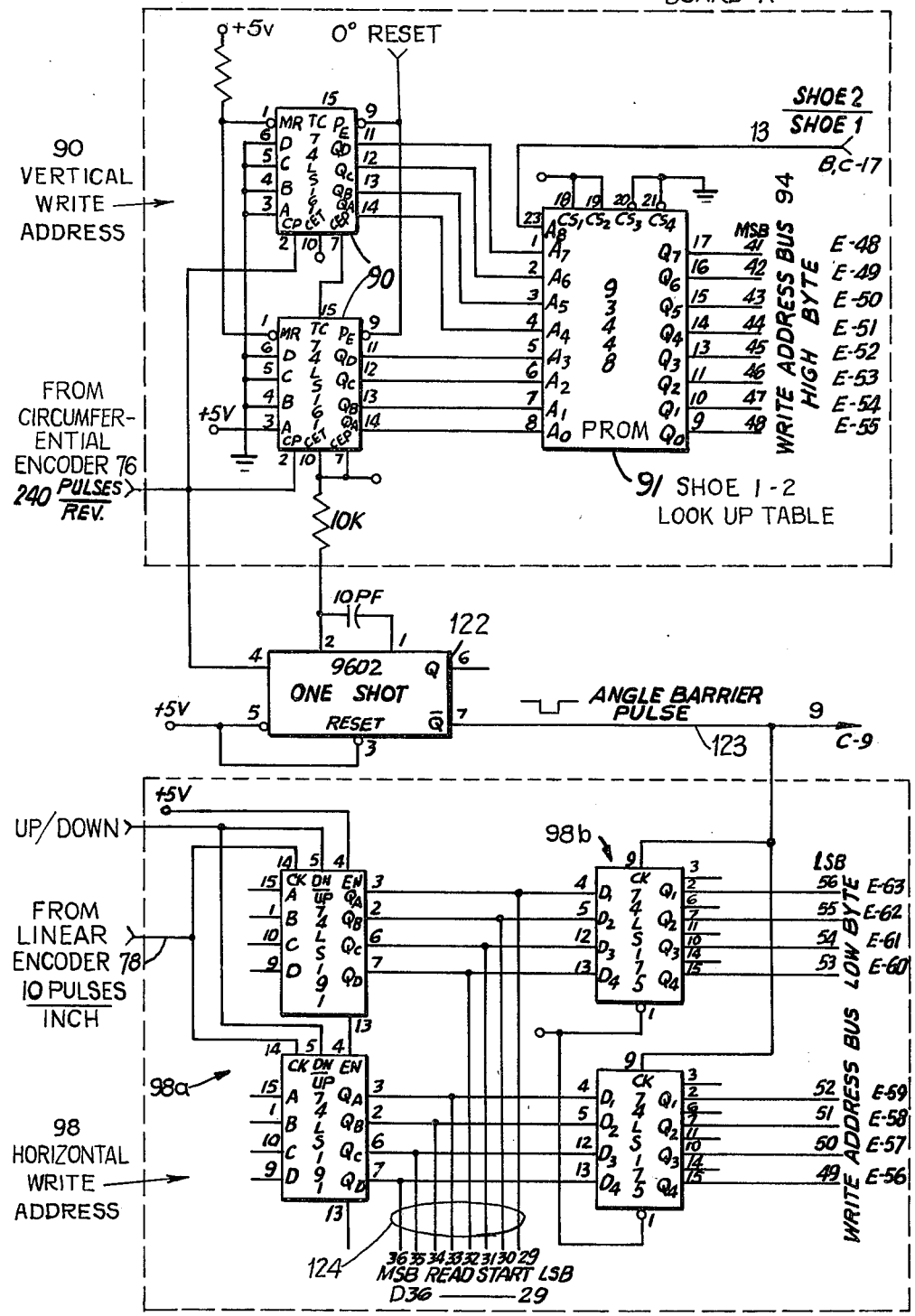
FIGS. 16-21 are more detailed wiring and schematic diagrams of the component portions of the system illustrated in FIG. 9.
Figure 17:
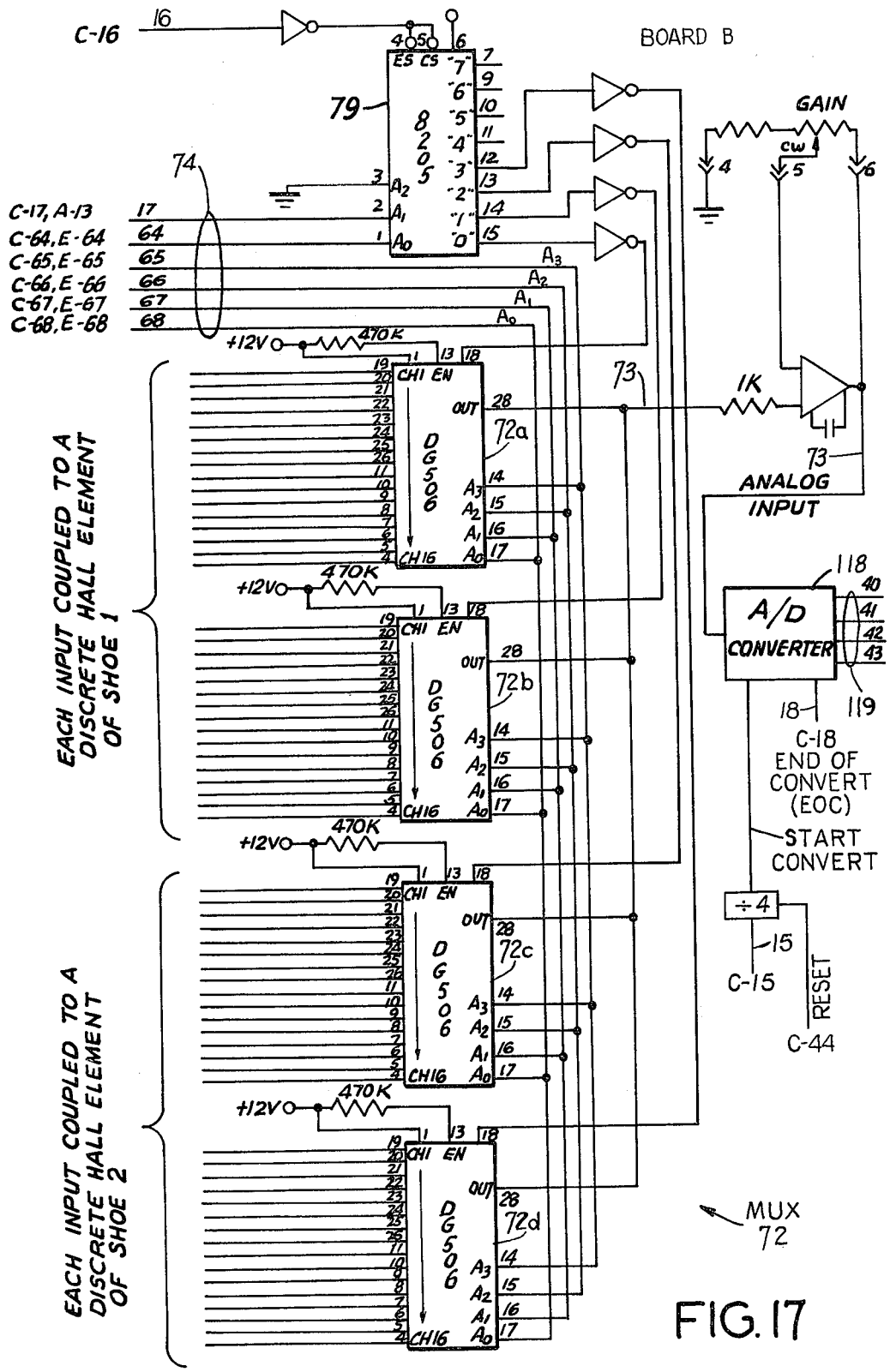

In FIG. 16, the 1.5° angular pulses from circumferential encoder 76 are coupled to vertical write address circuit 90 which is comprised of two 4 bit counters connected in tandem to provide an 8 bit counter. The counters are reset each time a 0° reset pulse occurs to indicate the 0° reference position of the rotating magnetic yoke of FIGS. 5 and 6. The counters count to a maximum of 240 before being reset.

The parallel output leads of vertical write address counters 90 are coupled to shoe 1-2 look-up table 91 which is a 512×8 bit field programmable ROM (PROM) that stores the sequentially occurring addresses from the counters. The coded shoe 1 - shoe 2 input on lead 13 adds, or programs, a count of 120 to the input from the counters when shoe 2 inspection signals are being sampled, as discussed above. The output of shoe 1-2 look-up table 91 is coupled out to board E on write address bus 94.

HORIZONTAL WRITE ADDRESS

Figure 20:
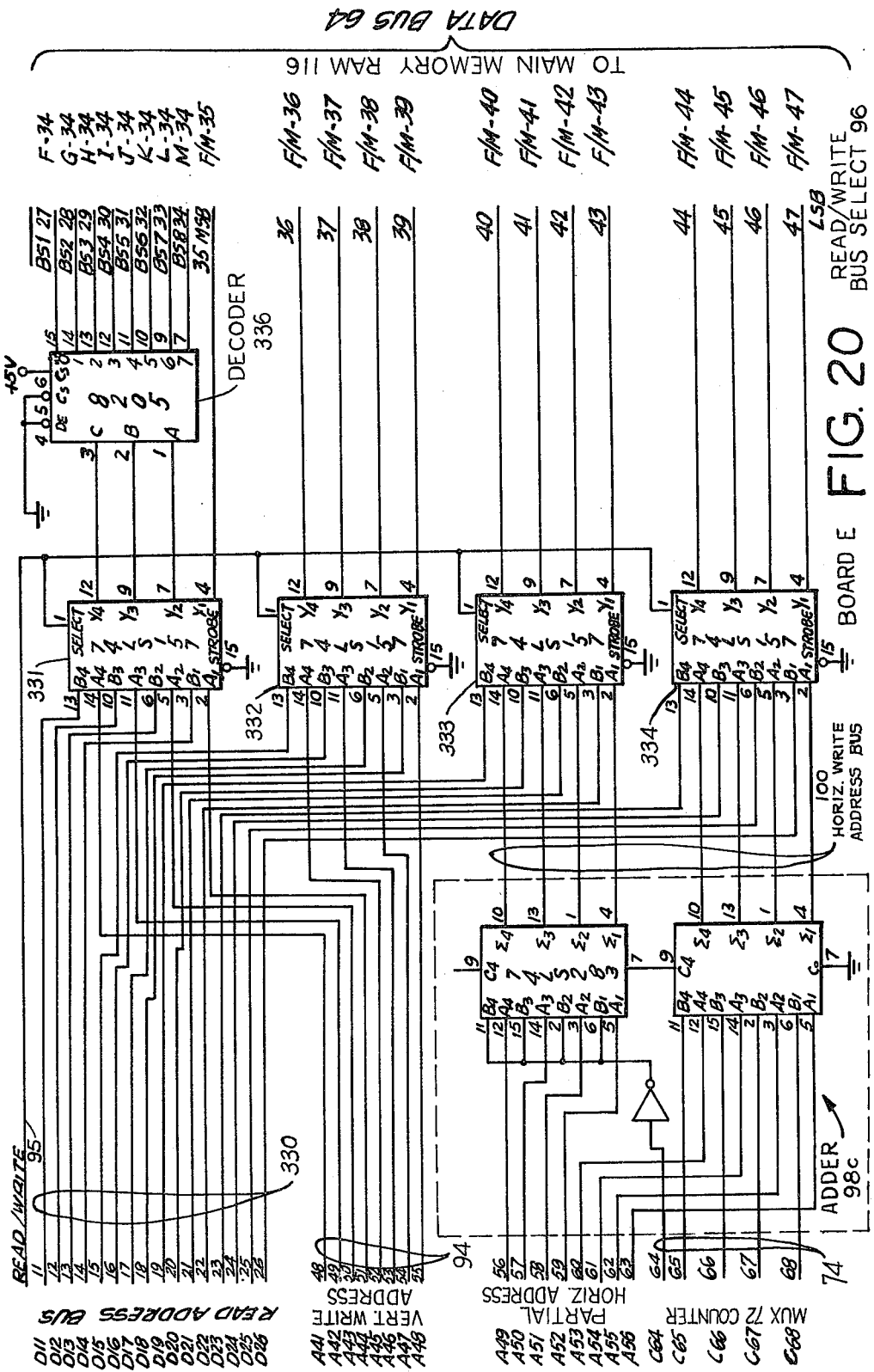

In FIG. 16, the horizontal write address circuit 98 is comprised of an 8 bit UP/DOWN counter 98a, data latches 98b, and an adder 98c that is on board E, FIG. 20. The one shot pulse generator 122 has its input pin 4 coupled to receive the angle pulses from the circumferential encoder 76. Its output on line 123 is coupled to the clock input pins 9 of the data latches 98b.

The incremental pulses from linear encoder 78 are coupled to UP/DOWN counter 98a which is two 74LS191 4 bit programmable counters connected in tandem. The signal level of the UP/DOWN input to counter 98a determines whether the counter counts up or down. The counter counts up when the pipe 10 of FIG. 6 advances in the forward direction through the inspection apparatus and counts down when the direction of pipe 10 is reversed to cause the pipe to "back up", as might be desirable if the operator wishes to take a second and closer look at a section of the pipe.

The output of counter 98a is coupled over bus 124 (leads 29-36) to read address generator 114 (also see FIG. 9). The output leads of counter 98a also are coupled to the inputs of data latches 98b. The output of counter 98a is loaded into latches 98b by each 1.5° angle barrier pulse that occurs on output lead 123 of one shot 122.

The output leads 49 through 56 of data latches 98b are connected to leads E-56 through E-63 in FIG. 20, these being input leads to adder 98c of the horizontal write address circuit 98.

64 CHANNEL MULTIPLEXER (MUX)

As indicated on the lower left side of FIG. 9, the 64 Hall effect elements, or detectors, each is coupled to a respective preamplifier 70 and the preamplifier outputs are coupled as corresponding inputs to the 64 channel multiplexer 72. Details of MUX 72 are shown on printed circuit board B, FIG. 17. MUX 72 is comprised of four 16 channel multiplexers 72a-72d. Multiplexers 72a and 72b receive the 32 output signals from respective Hall effect elements in shoe 1, and multiplexers 72c and 72d receive the output signals of the 32 Hall effect elements in shoe 2. Each of the multiplexers, in effect, has 16 addressable switches which are addressed by a 4 bit coded signal on its respective input terminals $A_0$, $A_1$, $A_2$ and $A_3$. An input inspection signal on an addressed input line is coupled to the single output line 73. The 4 bit coded address signals are coupled to MUX 72 on bus 74 which is the output signal from MUX control counter 92 and write control signal 93 that are on board C, FIG. 18.

A MUX enable signal on bus 74 from MUX control counter 92 is coupled to the input of a two-line to four-line decoder 79 to select one of the MUX devices 72a, 72b, 72c, or 72d. When one of these MUX devices is selected, its 16 input lines then are sequentially sampled and the sampled signals are coupled to output line 73. In this manner all 64 Hall effect devices of shoe 1 and shoe 2 are sequentially sampled. MUX 72 is comprised of conventional devices such as a 16 channel analog multiplexer device DG506 produced by Siliconix Corporation. Decoder 79 may be an 8205 1 out of 8 binary decoder available from Intel Corporation.

ANALOG-TO-DIGITAL CONVERTER

The multiplexed analog signals on output line 73 of MUX 72, FIG. 17, are coupled to analog-to-digital converter 118 which is a conventional device of the successive approximation type that converts an analog input signal to a 4 bit digital signal on output bus 119. This a/d converter may be similar to a TDC1014J device by TRW, Inc.

The operation of A/D converter 118 is controlled by the start convert signal that is received on its lead 15. The end of convert signal (EOC) is produced when the conversion process is completed. The EOC signal on lead 18 is coupled to input C-18 on board C, FIG. 18.

MULTIPLEXER CONTROL COUNTER, WRITE CONTROL CIRCUIT AND TEMPORARY MEMORY

Figure 18:
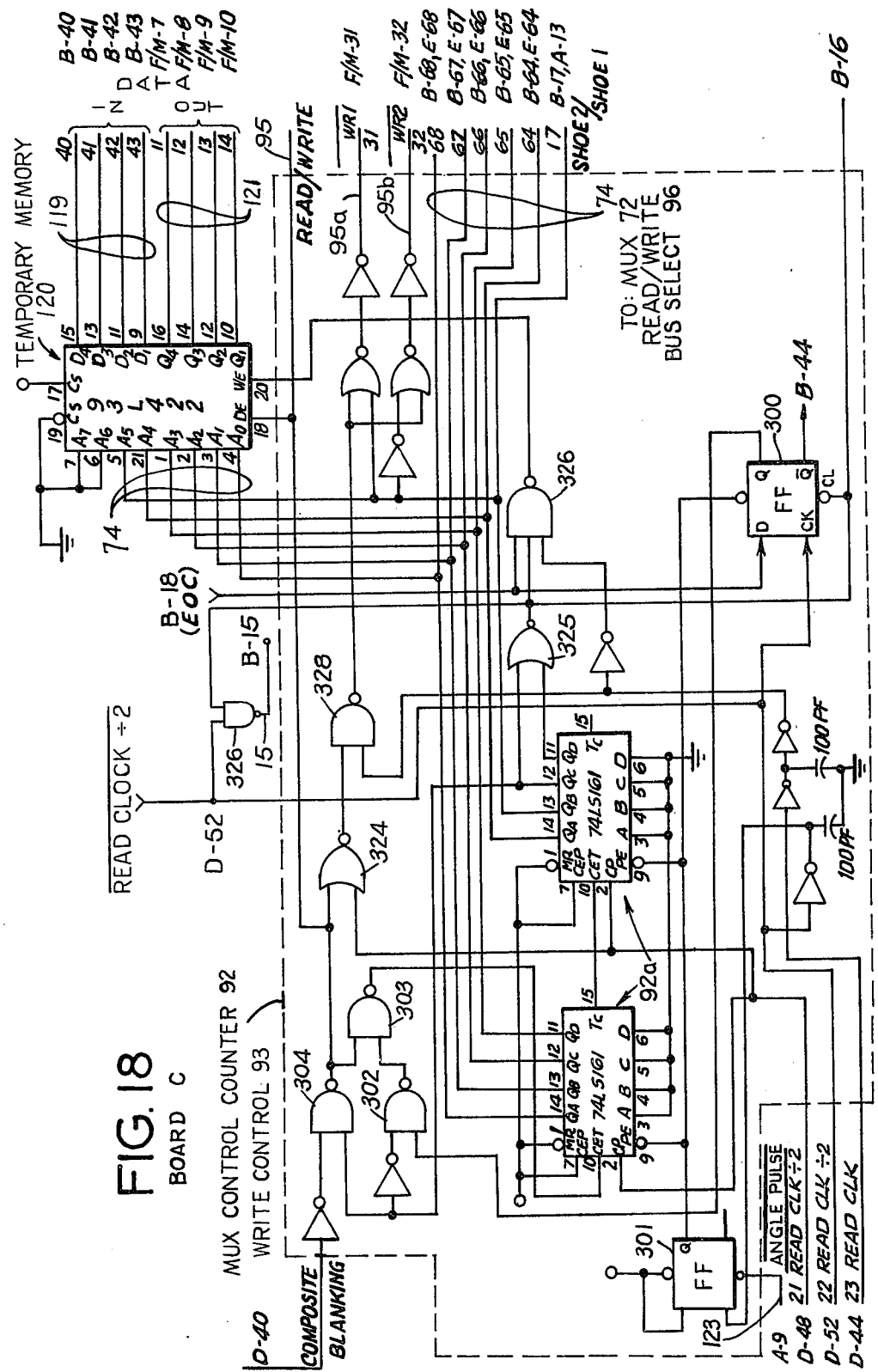

The MUX control counter 92 and write logic circuit 93 are on board C, FIG. 18, and are comprised of an 8 bit counter 92a and various other gating logic circuitry. Counter 92a counts clock pulses coupled in on lead D-48 and produces on its output bus 74 write address signals at a 0.5 MHz rate that control the sensing operation of 64 channel MUX 72 and the storing of the sensed signals in temporary memory 120. Address signals on bus 74 at a higher rate of approximately 2.0 MHz control the transfer of data from temporary memory 120 to main memory RAM 116. Address bus 74 also is connected to the inputs E-64 through E-68 of adder 98c on board E, FIG. 20.

D-type flip flop 301 receives an angle stroble pulse on input line 123 and produces a preset pulse on its Q output which presets both chips of counter 92a and presets flip flop 300 so its Q output is a one.

Assuming that the multiplexing operation is just commensing after an angle pulse on input lead 123 has been received, the output at pins 11 and 12 of the second chip of counter 92a are low and the output of NOR gate 325 is high. This high signal is coupled to NAND gate 326 at the top, center of FIG. 18, and permits read clock÷2 bar signals at approximately 2 MHz to pass through the gate. These signals are coupled to lead B-15, FIG. 17, at the input to A/D converter 118. These pulses are divided by 4 and cause converted digital data signals to be produced on output bus 119. At the conclusion of the conversion of each four bit nibble from A/D converter 118, and end of convert (EOC) signal is produced on lead 18. This signal, at a rate of 0.5 MHz, is coupled to lead C-18, FIG. 18 and is coupled to the data input of D-flip flop 300. The next occurring clock input pulse, a read clock÷2 pulse, is clocked through flip flop 300 and causes the Q output to go high. This high is coupled to one input of NAND gate 302 and the inverted low, a high, from pin 12 of the second counter chip is coupled to the other input of the NAND gate. Its output goes low and causes a high to be produced at the output of NAND gate 303. This high is coupled to pin 10 of the first counter chip and enables the chip. The next clock pulse on pin 2 of the chip adds a count of one to the counter. After the EOC pulse terminates, the Q output of flip flop goes low, and by way of the NAND gates 302-304, a low signal is produced at pin 10 of the first counter chip. The counter now will not count any of the clock pulses which are occurring at a 2.0 MHz rate.

The above described operation is repeated when the next EOC signal is coupled to the D input of flip flop 300. The result is that counter 92a counts at a 0.5 MHz rate during the multiplexing operation during which the 64 Hall elements are sampled.

The output of counter 92a is coupled over address bus 74 to temporary memory RAM 130 to cause the digital data on data bus 119 to be stored at addressed locations.

After 64 multiplexing samples have been completed the output of pin 12 of the second chip of counter 92a goes high. This is coupled through NOR gate 325 and appears as a low at the input of NAND gate 326 at the top of FIG. 18, thus disabling the passage therethrough of clock pulse÷2.

The high at pin 12 of the second counter chip also is coupled to NAND gate 304 at the upper left of the figure to pass composite blanking signals therethrough. This same high signal is inverted and applied to NAND gate 302. The other input to NAND gate 302 also is low since the Q output of flip flop 300 is low. The output of flip flop 302 therefore is high, and causes flip flop 303 to pass composite blanking pulses from flip flop 304. These are relatively long duration pulses at a rate of approximately 15.75 kHz, and when applied to pin 10 of the first chip of counter 92a cause the counter to count the clock input pulses at pin 2 which occur at a rate of 2.0 MHz. The lower stages of counter 92a therefore begin to count up again.

The high output of NAND gate 304 also is coupled to output lead 95 and serves as a read pulse to cause data stored in temporary memory 120 to be read out on bus 121 to main memory 116.

During this read operation, NAND gate 326 is passing clock pulses at a rate of 2 MHz to enable the reading of temporary memory 120 at the 2.0 MHz rate.

During this read operation the outputs of flip flop 300 that are coupled to leads B-16 and B-44 on board B, FIG. 17, serve as disable signals to disable, respectively, decoder 79 and A/D converter 118.

At the conclusion of the composite blanking signal counter 92a is disabled by a low on its pin 10. Q output of flip flop 300 is low because a clear signal is applied to its clear input (CL) from NOR gate 325. On the next occurrence of a composite blanking pulse counter 92a again is enabled at pin 10 and continues its count. When it finally reaches a count of 64 (after four horizontal blanking pulses or one vertical blanking pulse), pin 12 of the second counter chip goes low and pin 11 goes high. The logic circuitry at the upper left of FIG. 18 reverses condition and holds counter 92a disabled. It is noted that since pin 11 now is high, the output of NOR gate 325 still is low to hold flip flop 300 in its cleared state during which Q output is low. The counter remains in this condition until the next 1.5° angle pulse appears on input line 123 and actuates flip flop 301 which in turn resets counter 92a and flip flop 300. The circuitry now is in a write condition and the multiplexing operation commences, as described above.

READ ADDRESS GENERATOR

Figure 19A:
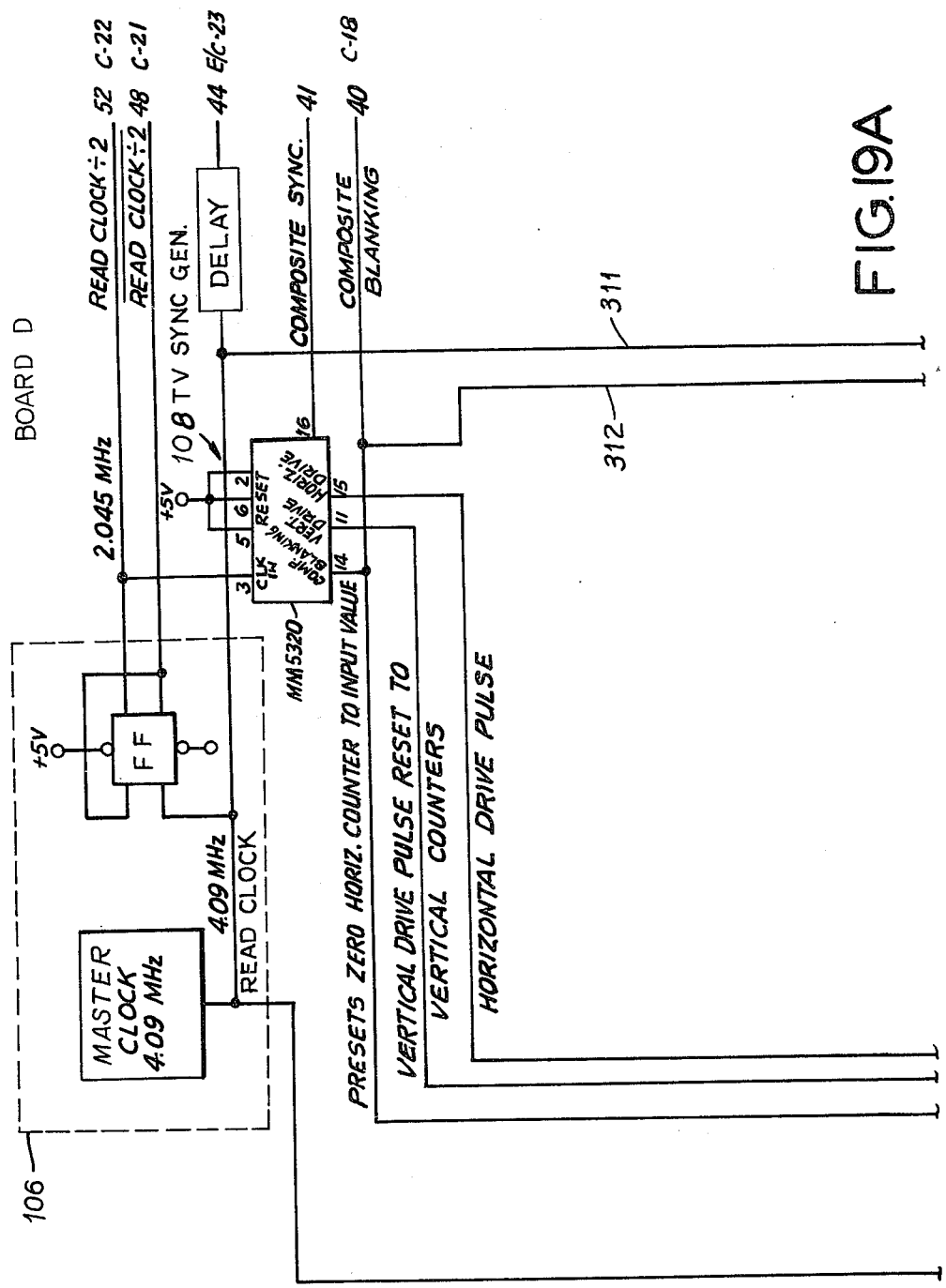
Figure 19B:
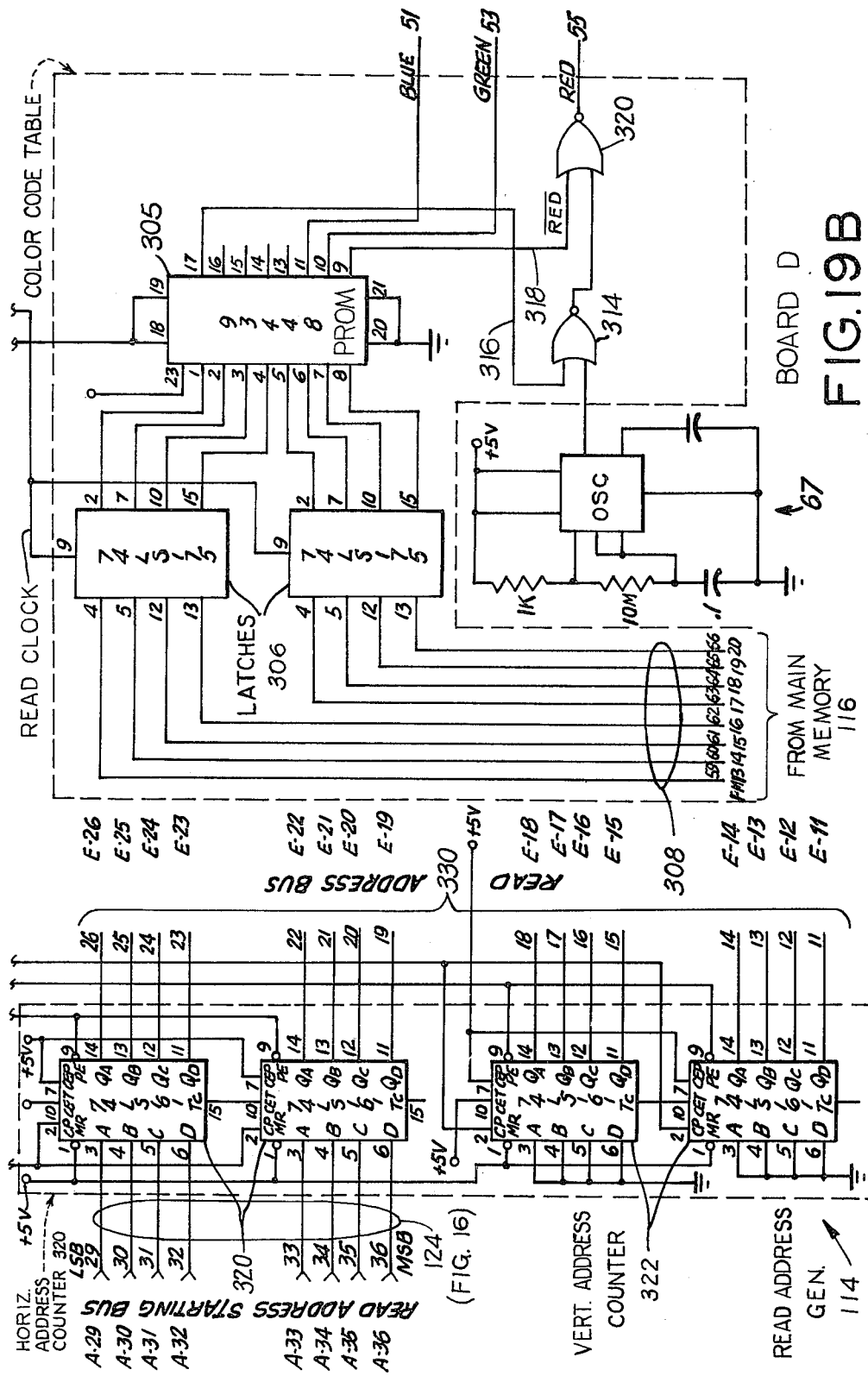

Read address generator 114 is illustrated on the left of FIG. 19B and is comprised of two presettable horizontal address counters 320 and two presettable vertical address counters 322. The inputs on lines 29 - 36 on horizontal address counters 320 connect to the up-/down counter 98a of horizontal write address counter 98, FIG. 16, by way of data bus 124. In effect, the address of the number 1 Hall probe of a designated shoe is loaded into horizontal address counter 320 each time a composite blanking signal is coupled to pins 9 of each of the two counter chips. The horizontal address counter 320 then commenses to count master clock pulses at the rate of 4.09 MHz. What this means in terms of reading data from main memory RAM 116 is that from the time of occurrence of each composite blanking signal the data corresponding to Hall effect probe 1 of shoe 1 is read out of main memory RAM 116 and then the horizontal address of each successive adjacent linearly extending incremental region is read from main memory until the counter is reset after counting to 220. In this way the TV display always begins with the current position of the first Hall probe in shoe 1 and successively displays up to 220 adjacent incremental regions that are horizontally aligned. The 220 count is the count in the horizontal address counter 320 before it is reset by a composite blanking signal.

If the pipe is reversed in its direction of movement through the inspection apparatus, UP/DOWN counter 98a in horizontal write address circuit 98 will count down so as to cause the linear addresses to "back up" as the pipe continues in the reverse direction. These "back up" addresses are the addresses initially loaded into horizontal address counters 320, FIG. 19b each time a composite blanking signal occurs in the TV sync generator 108 of FIG. 19a. Because of this type of operation the TV display always follows the motion of the pipe relative to the inspection apparatus.

Vertical address counter 322 in read address generator 114 counts up in response to the horizontal drive pulses from TV sync generator 108 and are reset in response to each vertical drive pulses from sync generator 108.

The outputs of the horizontal address counter 320 and the vertical address counters 322 are coupled over read address bus 330 to read/write bus select circuit 96, FIG. 20. The counters in read address generator 114 may be 74LS161 counters, for example.

READ/WRITE BUS SELECT

Read/write bus select circuit 96 is on printed circuit board E, FIG. 20, and includes four two lines-to one line multiplexers 331, 332, 333 and 334, and a 1 out of 8 decoder 336. The inputs to read/write bus select circuit 96 are on the left of the figure and are comprised of the read address codes on bus 330, the vertical write address codes on bus 94, and the horizontal write address codes on bus 100. As previously explained, bus 100 is the output of adder 98C which is part of the horizontal write address circuit 98, FIG. 9. Each of the multiplexer circuits 331-334 operates in response to a strobing read/write signal on line 95 to select either a read input address or a write input address that is coupled to its input. The selected input address is coupled to the respective four output lines of each multiplexer device 331-334.

Decoder 336 receives a coded input signal from multiplexer 331 and in response thereto selects a designated one of its eight output lines. The selected output lines are in fact select lines for selecting one of the eight printed circuit boards F-M that comprise main memory RAM 116. The outputs of multiplexers 332, 333, 334 are connected to the respective lines indicated by the numerals to each one of the eight memory boards F-M. Thus, the output of decoder 336 selects the memory board and the output lines 36-47 of the multiplexers 332-334 energize the respective input leads to the selected memory board.

The multiplexers may be of the type 74LS157, and decoder 336 may be an Intel 8205 binary decoder.

MAIN MEMORY RAM

Figure 21A:
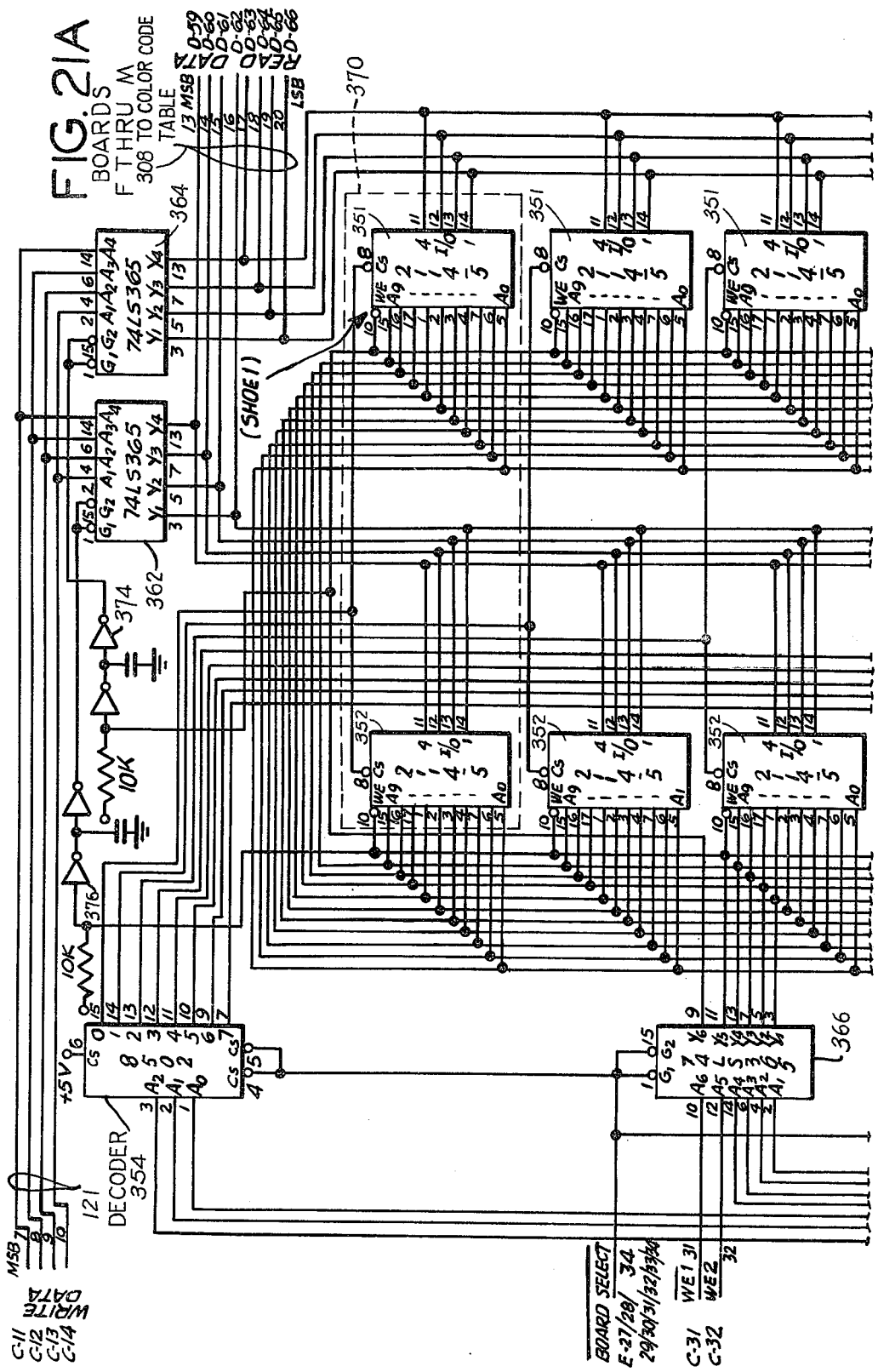
Figure 21B:
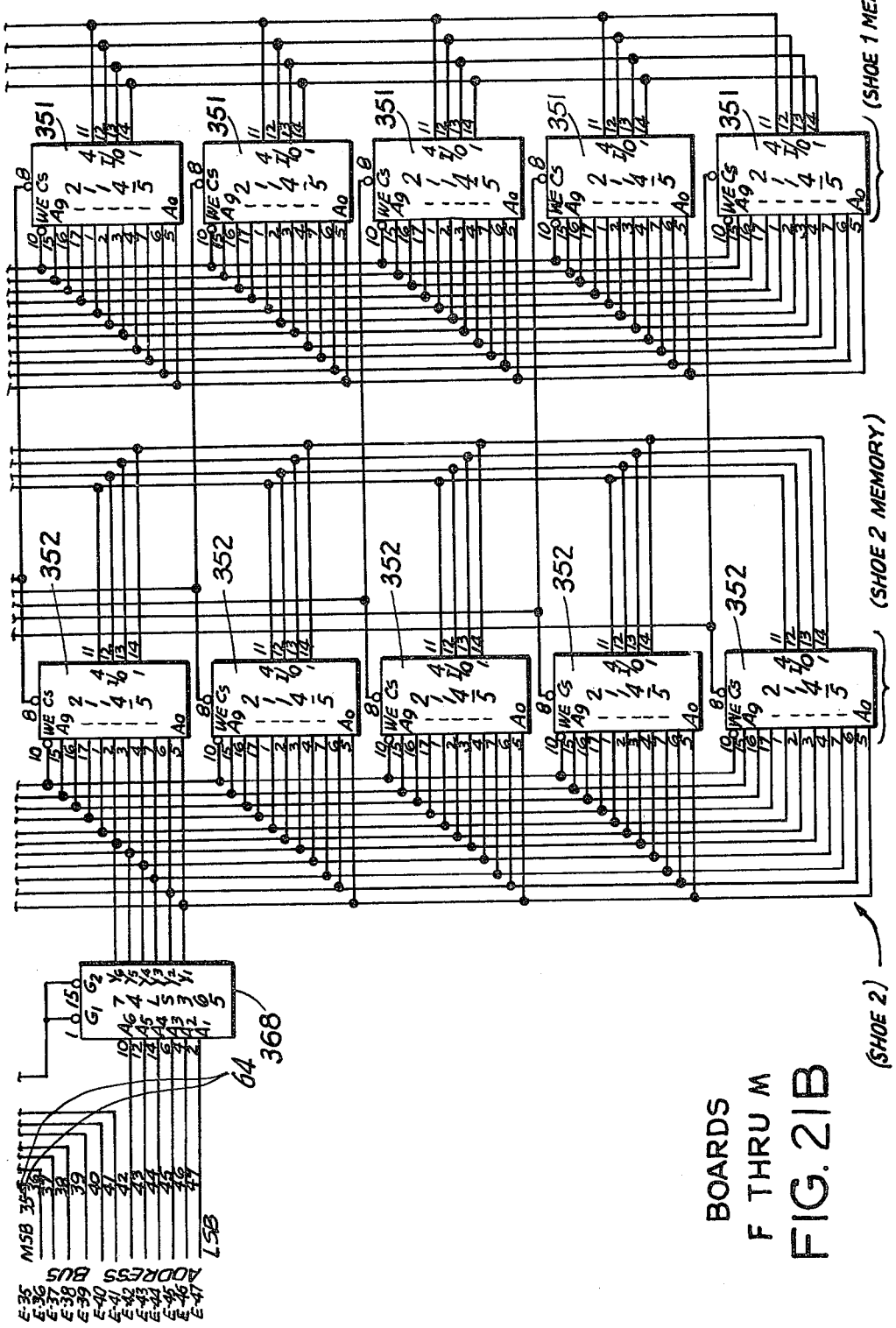

The main memory RAM 116 is comprised of eight printed circuit boards F-M, FIGS. 21a and 21b. The eight memory boards F-M provide 64K by 4 bits of memory for each one of the search shoes. As seen in FIGS. 21a and 21b each memory card has eight 1024×4 bit RAM chips 351 associated with search shoe one and eight 1024×4 bit RAM chips 352 associated with search shoe two. Each memory board also includes 1 out of 8 binary decoder 354, buffer circuits 362, 364, 366 and 368, and associated gating logic. Because the eight memory boards are indentical only one is illustrated and described. As was explained above, the memory board F-M that is to be selected is addressed by decoder 336 of the read/write bus select circuit 96, FIG. 20. The board select coded signals are coupled in on bus 64 at the left of FIGS. 21a and 21b.

The 1 out of 8 decoder 354 receives a three bit coded signal on bus 64 from read/write bus select circuit 96, FIG. 20. This coded input is decoded to select one of the eight output lines of decoder 354. The selected output line of decoder 354 in turn selects a respective pair of the eight pairs of shoe 1 and shoe 2 RAM circuits 351 and 352. For example, in FIG. 21a the pair of RAM circuits 370 shown in the broken line rectangle are selected by the output of pin 15 of decoder 354.

The address location in each RAM chip 351 and 352 is selected by coded address signals on address bus 64 which is the output of read/write bus select circuit 96, FIG. 20.

The data input to the pairs of RAM chips 351 and 352 are coupled to main memory RAM 116 on write data bus 121 from temporary memory 120, FIG. 18. Bus 121 (upper left of FIG. 21a) is coupled to buffers 362 and 364 which are respectively energized according to whether data from shoe 1 or shoe 2 is being received on write data bus 121. That is, buffer 362 or 364 is selected by respective gating circuit 374 or 376, which in turn operate in response to write enable signals WE1 or WE2 that are produced on board C, FIG. 18, and which are coupled to the memory board on the left of FIG. 21a. Each of the RAM chips 351 and 352 stores a plurality of 4 bit nibbles that correspond to the magnitudes of the inspection signals detected by Hall effect elements in shoe 1 and shoe 2 when two Hall effect elements were inspecting the same incremental region of the pipe surfaces.

The data read from the pairs of RAM chips 351 and 352 is coupled out on bus 308 to the color code table 130, FIG. 19b.

COLOR CODE TABLE

Color code table 130 is on printed circuit board D, FIG. 19b. Data stored in main memory RAM 116 is transferred on bus 308 to latches 306 at the read clock rate of 4.09 MHz. The data on bus 308 is the two 4 bit nibbles of the type illustrated in FIG. 10, these nibbles corresponding to the magnitudes of the two inspection signals that were detected by shoes 1 and 2 at the same incremental region on pipe 10. These two nibbles come from an addressed pair of RAM chips 351 and 352 in FIG. 21a. The output of latches 306 is coupled to PROM 305 and is addressed to a location having the identical code. In accordance with the relationships set forth in the Color Code Table that is set forth above, a respective one or more of the blue/green, and/or red output lines are energized to energize a corresponding gun(s) in the color TV monitor 65 of FIG. 9.

In the Color Code Table set forth above it is seen that a flash signal is indicated when the color red is to be displayed. The red display is used to indicate the most severe anomalies, and this red color is flashed on and off to better assure that the operator is alerted to the existance of the severe anomalies. In FIG. 19b a low frequency oscillator 67 provides an oscillating signal to NOR gate 314. The other input lead 316 to the NOR is an enable signal that causes NOR gate 314 to pass the oscillating signal, thereby turning NAND gate 320 on and off and modulating the red signal that is coupled on line 318 to NOR gate 320.

VIDEO MONITOR

The video monitor 65, FIG. 9 is connected to the red, green, blue output lines of color code table 130. Color monitor 65 also is coupled to receive the conventional timing and sync signals TV sync generator 108.

In the manner explained, improved inspection results are obtained by inspecting each incremental region of the pipe with perpendicularly directed magnetic fields and combining the magnitudes of the two inspection signals received from each incremental region. These combined signals then are color coded according to magnitude and then displayed to show the color of each incremental region. Not only is greater accuracy achieved in actually detecting anomalies in a pipe wall, but these detected anomalies are displayed with more definition and meaning than heretofore attainable.

In FIGS. 16–21 of the drawings the integrated circuit chips or packages are identified by their designation numbers directly on the drawings. The illustrated logic devices may be any suitable devices that will perform the indicated logic function, or its equivalent.

In its broader aspects, this invention is not limited to the specific embodiment illustrated and described. Various changes and modifications may be made without departing from the inventive principles herein disclosed.

While a preferred embodiment of the invention has been illustrated and described, it is to be understood that alterations and modifications may be made to the described embodiment without departing from the scope of the present invention.

I claim:

1. The method of nondestructively inspecting a member of magnetic material comprising the steps, establishing a first steady magnetic field component in a first direction through a given incremental region of the member, establishing through said incremental region a second steady magnetic field component in a direction substantially transverse to said first direction, detecting the magnitude of said first magnetic field component at the surface of said incremental region and producing a first signal in response thereto, detecting the magnitude of said second magnetic field component at the surface of said incremental region and producing a second signal in response thereto, combining the magnitudes of said first and second signals to obtain the sum thereof, producing in response to said combined signals a representation of the magnitude of the combined signals.

2. A method for nondestructively inspecting a magnetic member comprising the steps, establishing in a first time period a first steady magnetic field component in a first direction through a given incremental region of the member, detecting during said first time period the magnitude of said first magnetic field component at the surface of the member adjacent said incremental region and producing in response thereto a first inspection signal, establishing during a second time period through said incremental region a second steady magnetic field component in a direction transverse to said first direction, detecting during said second time period the magnitude of said second magnetic flux component at the surface of the member adjacent said incremental region and producing in response thereto a second inspection signal, combining the magnitudes of said first and second inspection signals, and displaying and/or recording signals corresponding to said combined inspection signals to provide an indication of the magnitude thereof.

3. The method claimed in claim 2 wherein the step of combining the magnitudes of said first and second inspection signals includes the steps, storing said first inspection signal during said first time period, storing said second inspection signal during said second time period, and operating on said stored inspection signals to provide a display or record thereof that is representative of the magnitude of the combined inspection signals.

4. The method claimed in claim 2 wherein the steps of establishing said first and second steady magnetic field components is comprised of the steps, establishing said first magnetic field component in said member by means of magnetic field establishing means having at least two magnetic poles whose positions are changeable relative to said incremental region, changing the positions of said two magnetic poles of the magnetic field establishing means relative to said incremental region to establish therebetween said second steady magnetic field component in a direction transversely to the first magnetic field component.

5. The method claimed in claim 3 and further including the steps, producing during said first and second time periods address signals that are representative of the location of said incremental region of said member, displaying and/or recording said address signals with said combined inspection signals to provide an indication of the location of the incremental region on said member as well as an indication of the magnitude of the combined inspection signals detected at said incremental region.

6. The method claimed in claim 5 wherein the displaying step includes the further step, producing color signals in response to combined inspection signals wherein at least three different ranges of magnitudes of inspection signals correspond to three different color signals, and coupling said color signals and said address signals to color display means having at least three different color capabilities and thereby displaying said combined inspection signals in colors corresponding to their respective magnitudes.

7. A method of nondestructively inspecting an elongated tubular member of material comprising the steps, establishing in a first time period a first steady magnetic field component in a first direction through a given incremental region of the tubular member wall, detecting during said first time period the magnitude of said first magnetic field component at the surface of said incremental region and producing a first inspection signal in response thereto, establishing through said given incremental region during a second time period a second steady magnetic field component in a direction transverse to said first direction, detecting during said second time period the magnitude of said second magnetic field component at the surface of said incremental region and producing in response thereto a second inspection signal, combining said two inspection signals to obtain a composite signal corresponding to the magnitude of the combined signal, and displaying and/or recording said composite signal with an indication of the magnitude thereof.

8. The method claimed in claim 7 and further including the steps of, producing address signals during the detecting of said first and second magnetic field components to represent the location of said incremental region on the tubular member wall, including in said display and/or record of the composite inspection signal a representation of at least a portion of said tubular member wall and a representation of the location of said incremental region thereon.

9. The method claimed in claim 8 wherein the displaying step includes the further step, producing color signals in response to said composite signals wherein at least three different ranges of magnitudes of composite signals correspond to three different color signals, and coupling said color signals and said address signals to color display means having at least three different color capabilities and thereby displaying said composite signals in colors corresponding to their respective magnitudes.

10. A method of nondestructively inspecting a member of magnetic material comprising the steps, establishing a first steady magnetic field component in a first direction through a given incremental region of the member, detecting the magnitude of said first magnetic field component at the surface of said incremental region, establishing through said incremental region a second steady magnetic field component in a direction transverse to said first direction, detecting the magnitude of said second magnetic field component at the surface of said incremental region, combining the magnitudes of said detected first and second magnetic field components, producing address signals representative of the location of said incremental region on said member during the detecting of said first and second magnetic field components thereat, and producing in response to the combined magnitudes of the detected magnetic field components and to said address signals a visual presentation that represents the location of said incremental region on the tubular member and represents at least the magnitudes of combined detected magnetic field components that exceed a predetermined magnitude.

11. A method of nondestructively inspecting a member of magnetic material comprising the steps, establishing a first steady magnetic field component in a first direction through a given incremental region of the member, establishing through said incremental region a second steady magnetic field component in a direction substantially transverse to said first direction, detecting the magnitude of said first magnetic field component at the surface of said incremental region and producing a first signal in response thereto, detecting the magnitude of said second magnetic field component at the surface of said incremental region and producing a second signal in response thereto, combining the magnitudes of said first and second signals to produce a resultant signal whose magnitude is the sum of the combined signals, producing address signals representative of the location of said incremental region on said member during the detection of said first and second magnetic field components, and producing in response to said resultant signal and said address signals a representation of the location of said incremental region on said member and the magnitude of the resultant signal.

12. The method claimed in claim 11 wherein the displaying step includes the further step, producing color signals in response to said combined signals wherein at least three different ranges of magnitudes of combined signals correspond to three different color signals, and coupling said color signals and said address signals to color display means having at least three different color capabilities and thereby displaying said combined signals in colors corresponding to their respective magnitudes.

13. A method of nondestructively inspecting an elongated tubular member of magnetic material comprising the steps, establishing in a first time period a first steady magnetic field component in a first direction through a given incremental region of the tubular member wall, detecting during said first time period the magnitude of said first magnetic field component at the surface of said incremental region and producing in response thereto a first inspection signal, establishing through said given incremental region during a second time period a second steady magnetic field component in a direction substantially transverse to said first direction, detecting during said second time period the magnitude of said second magnetic field component at the surface of said incremental region and producing in response thereto a second inspection signal, combining the magnitudes of said first and second inspection signals, producing address signals representative of the location of said incremental region on said tubular member, producing in response to said address signal and said combined inspection signals a display and/or record that establishes the location of said incremental region on the tubular member and provides a representation at the recorded location of said incremental region the combined magnitudes of said inspection signals.

14. The method claimed in claim 13 wherein the steps of establishing said first and second transversely directed steady magnetic field components is comprised of the steps, establishing said first magnetic field component in said tubular member wall by means that includes a rotatable magnetic field establishing means that is positioned at a first circumferential location about said tubular member at said first time period, and rotating said magnetic field establishing means from said first location to a second circumferential location at said second time period.

15. The method claimed in claim 14 the steps of establishing said first and second magnetic field components includes the step of establishing a steady magnetic field component in the axial direction in the region of the wall of the pipe where the transversely directed magnetic field is present.

16. The method claimed in claim 15 wherein the displaying step includes the further step producing color signals in response to combined inspection signals wherein at least three different ranges of magnitudes of inspection signals correspond to three different color signals, and coupling said color signals and said address signals to color display means having at least three different color capabilities and thereby displaying said combined inspection signals in colors corresponding to their respective magnitudes.

17. The method of nondestructively testing a member comprising the steps, establishing relative motion between said member and an anomaly inspection means that is adjacent the surface of said member and deriving a succession of electrical inspection signals whose magnitudes are representative of a characteristic of a respective succession of contiguous incremental regions of said member, simultaneously generating address signals corresponding to the positions of said succession of incremental regions when said inspection means are at said succession of incremental regions, storing said succession of inspection signals at respective storage locations that are defined in a storage means by respective address signals which correspond to respective incremental regions on said member from which said succession of inspection signals originated, reading the inspection signals stored in said storage means and converting the magnitudes of the read inspection signals to color coded signals wherein predetermined different codes of the color coded signals represent respective different ranges of magnitudes of said inspection signals, displaying signals corresponding to the color coded signals on color display means at locations thereon corresponding to the locations of the succession of incremental regions, thereby to present a color coded pictorial representation of the location and magnitude of said characteristic of incremental regions of said member.

18. Apparatus for nondestructively inspecting a member of magnetic material, comprising means for establishing a first steady magnetic field component in a first direction through a given incremental region of the member, means for establishing through said incremental region a second steady magnetic field component in a direction substantially transverse to said first direction, means for detecting the magnitude of said first magnetic field component at the surface of said incremental region and for producing a first signal in response thereto, means for detecting the magnitude of said second magnetic field component at the surface of said incremental region and for producing a second signals in response thereto, means for combining the magnitudes of said first and second signals to obtain the sum thereof, means for producing in response to said combined signals a representation of the magnitude of the combined signals.

19. Apparatus for nondestructively inspecting a member of magnetic material comprising, means for establishing a first steady magnetic field component in a first direction through a given incremental region of the member, means for establishing through said incremental region a second steady magnetic field component in a direction substantially transverse to said first direction, means for detecting the magnitude of said first magnetic field component at the surface of said incremental region and for producing a first signal in response thereto, means for detecting the magnitude of said second magnetic field component at the surface of said incremental region and for producing a second signal in response thereto, means for combining the magnitudes of said first and second signals to obtain the sum thereof, means for producing address signals representative of the location of said incremental region on said member during the detection of said first and second magnetic field components, and means for producing in response to said combined signals and said address signals a representation of the location of said incremental region on said member and the magnitude of the combined signals that were detected at said region.

20. Apparatus for nondestructively inspecting a magnetic member, comprising means for establishing in a first time period a first steady magnetic field component in a first direction through a given incremental region of the member, means for detecting during said first time period the magnitude of said first magnetic field component at the surface of the member adjacent said incremental region and producing in response thereto a first inspection signal, means for establishing through said incremental region during a second time period a second steady magnetic field component in a direction transverse to said first direction, means for detecting during said second time period the magnitude of said second magnetic field component at the surface of the member adjacent the incremental region and producing in response thereto a second inspection signal, means for combining the magnitudes of said first and second inspection signals to obtain the sum thereof, and means for displaying and/or recording signals corresponding to said combined inspection signals to provide an indication of the magnitude thereof.

21. The apparatus claimed in claim 20 wherein the means for combining the magnitudes of said first and second inspection signals includes, means for storing said first inspection signal during said first time period, means for storing said second inspection signal during said second time period, and means for operating on said stored inspection signals to provide said combined inspection signals for display and/or recording that are representative of the magnitude of the combined signals.

22. The apparatus claimed in claim 21 and including means for producing during said first and second time period address signals that are representative of the location of said incremental region of said member, and means responsive to said address signals and said combined inspection signals for producing signals suitable for display and/or recording to provide an indication of the location of the incremental region on said member as well as an indication of the magnitude of the combined inspection signals detected at said incremental region.

23. The apparatus claimed in claim 22 wherein said magnetic member is an elongated tubular member and said apparatus further includes, means for establishing relative longitudinal and circumferential motion between said tubular member and said two means for detecting said respective magnetic field components and said means for establishing said two magnetic field components, said means for establishing relative motion and said means for detecting said magnetic field components being so constructed and operated to cause each of said means for detecting magnetic field components to cover the same contiguous incremental regions of the tubular member.

24. The apparatus claimed in claim 23 wherein each of said means for detecting a magnetic field component comprises a plurality of closely spaced magnetic flux sensing means aligned parallel to the axis of said tubular member, said apparatus further including means for sequentially sampling the output of each of the sensing means of said first and then the second means for detecting magnetic flux components, said means for producing address signals operating in synchronism with the sampling of said sensing means for producing a respective address signal corresponding to the location on the pipe of each one of said sensing means when the sensing means is sampled, said means for producing the address signals also operating on said means for storing the inspection signals to cause the inspection signals to be stored at address locations corresponding to the incremental regions on the pipe from which the signals originated.

25. The combination claimed in claim 24 wherein said means for storing said inspection signals includes means for storing inspection signals emanating from the same incremental region at adjacent storage locations that comprise a stored information word, means for reading said stored information words, means responsive to said read stored words for providing respective display and/or recording signals that correspond to predetermined ranges of magnitudes of combined inspection signals that comprise said read words.

26. The apparatus claimed in claim 25 and further including color display means responsive to said display or recording signals for displaying said stored words as predetermined colors as determined by the magnitudes of the stored words.

27. The combination claimed in claim 25 wherein said means for reading stored information words includes read address generating means, comprising a first counting means adapted to receive on command a coded address signal representing the present longitudinal position on the tubular member of an end one of said plurality of flux sensing means of a given magnetic field detecting means, Clock pulse means coupled to said counting means for changing the count in said counter to provide longitudinal addresses of the remainder ones of the flux sensing means of said given magnetic field detecting means, and means for providing an address signal comprised of the contents of said counter, means for periodically resetting said counting means to synchronize the reading of said counting means with the operation of said display and/or recording means.

28. The combination claimed in claim 27 wherein said first counting means is always reset to the then present address of said end one of the flux sensing means, whereby the address in said counting means continually follows the position of said end one of the flux sensing means relative to said tubular member.

29. The combination claimed in claim 28 including second counting means for receiving on command the present circumferential position of said given magnetic field detection means, second clock pulse means coupled to said second counting means for incrementing the count in said second counting means to provide addresses of successive adjacent circumferential locations about said tubular member, means for providing an address signal comprised of the contents of said second counting means, and means for periodically resetting said second counting means to synchronize the reading of the second counting means with the operation of said display and/or recording means and with the relative motion between the tubular member and said magnetic field detecting means.

30. Apparatus for nondestructively testing a member comprising means for establishing relative inspection motion between said member and an anomaly inspection means that is adjacent the surface of said member, means for deriving a succession of electrical inspection signals whose magnitudes are representative of a characteristic of a respective succession of contiguous incremental regions of said member, means for simultaneously generating address signals corresponding to the positions of said succession of incremental regions when said inspection means are at said succession of incremental regions, means for storing said succession of inspection signals at respective storage locations that are defined in a storage means by respective ones of said address signals which correspond to respective incremental regions on said member from which said succession of inspection signals originated, means for reading the inspection signals stored in said storage means, means for converting the magnitudes of the read inspection signals to color coded signals wherein predetermined different codes of the color coded signals represent respective different ranges of magnitudes of said inspection signals, means for displaying signals corresponding to the color coded signals on color display means at locations thereon corresponding to the locations of the succession of incremental regions on the member, thereby to present a color coded pictorial representation of the location and magnitude of said characteristic of said incremental regions of said member.

31. The apparatus claimed in claim 30 wherein the means for reading the inspection signals stored in said storage means includes read address generating means, comprising counting means adapted to receive on command a coded address signal corresponding to the position in a first direction on the member of one of said incremental regions being inspected by said means for deriving the inspection signals, clock pulse means coupled to said counting means for changing the count in said counter to provide the addresses of incremental regions that are successively adjacent in said first direction, means for coupling address signals from said counting means, means for periodically resetting said counting means to synchronize the reading of the counting means with said display means and with the relative movement of the member and the inspection means.

32. The apparatus claimed in claim 31 wherein said counting means is always reset to the then present address of a predetermined incremental region then being inspected by the inspection means, whereby the address in said counting means continually follows the position of the inspection means relative to said member.

33. The combination claimed in claim 32 including second counting means for receiving on command the coded present address of said one incremental region in a second direction on said member, clock pulse means coupled to the second counting means for changing the count in said second counting means to provide addresses of incremental regions that are successively adjacent in said second direction said one region, and means for periodically resetting said second counting means to synchronize the reading of the second counting means with said means for displaying signals and with the relative motion between the member and said inspection means.

34. Apparatus for nondestructively inspecting an elongated tubular member of magnetic material, comprising magnetic field means for establishing a unidirectional magnetic field in a first direction through each one of given incremental regions in the wall of said tubular member, means for establishing relative longitudinal and rotary motion between said magnetic field means and said tubular member, said magnetic field means including means for establishing a magnetic field component directed substantially transversely to the axis of said member so that upon relative rotation between the tubular member and the magnetic field means said unidirectional magnetic field is established through said incremental regions in a second direction that is transverse to said first direction, first magnetic field sensing means relatively rotatable with respect to said tubular member for sensing the unidirectional magnetic field adjacent the wall at said incremental regions of the tubular member when the unidirectional magnetic field is in said first direction through the incremental regions, second magnetic field sensing means relatively rotatable with respect to said tubular means for sensing the unidirectional magnetic field adjacent the wall of said incremental regions of the tubular member when said unidirectional magnetic field is in the second direction through the incremental region, each one of said magnetic field sensing means providing substantially the same inspection coverage of the wall of said tubular member, each of said magnetic field sensing means producing a respective inspection signal upon detecting an anomaly in an incremental region, the magnitudes of said inspection signals being a function of the magnitude and/or severity of said anomaly, means providing address signals corresponding to the axial and circumferential locations of said first and second magnetic field sensing means with respect to said tubular member, storage means responsive to said address signals and said inspection signals for storing said inspection signals at respective address locations corresponding to the axial and circumferential locations on the tubular member where respective inspection signals originate, means operating on said stored inspection signals for providing a visual presentation thereof, said inspection signals appearing on the visual presentation at locations that correspond to respective incremental regions on the tubular member from which the signals originated and with a display indicia corresponding to the summation of the inspection signals produced by the magnetic field sensing means when sensing said unidirectional magnetic fields at the corresponding incremental region.

35. Apparatus for nondestructively inspecting an elongated tubular member of magnetic material, comprising a first magnetic field producing means adapted to establish a longitudinally directed steady magnetic field component in the wall of a tubular member, second magnetic field producing means for establishing a transversely directed steady magnetic field component in the wall of said tubular member, said longitudinal and transverse magnetic field components being coincidence in time and space in the wall of the tubular member and producing therein a resultant magnetic field component, means for rotating said second magnetic field establishing means about the longitudinal axis of said tubular member, whereby said transverse magnetic field component is directed in an opposite transverse direction when the second magnetic field establishing means is rotated a predetermined angle, the oppositely directed transverse magnetic field component combining with the longitudinally directed magnetic field component in said tubular member to produce a second resultant magnetic field component that is transverse to the first resultant magnetic field component, means for establishing relative longitudinal motion between said two magnetic field establishing means and said tubular means, first and second magnetic field detector means angularly spaced about the surface of said tubular member, and rotatable with said second magnetic field producing means for sensing said first and second resultant magnetic field components adjacent the wall of said tubular member, each of said detector means including a plurality of axially aligned magnetic sensing means for sensing respective contiguous incremental regions of the wall of said tubular member, each of said sensing means being operable to produce an inspection signal upon detecting an anomaly in a respective incremental region being inspected, said detector means being rotatable about the surface of said tubular member in such a manner and at a rotational rate that assures that said detector means provides substantially the same inspection coverage of the wall of said tubular member, means for sequentially sampling said plurality of sensing means of said first detector means and then sequentially sampling the sensing means of said second detector means, means for producing address signals representing the circumferential and longitudinal positions of each one of said sensing means as the sensing means are sequentially sampled, storage means for storing sampled inspection signals at storage locations corresponding to the addresses of the respective sensing means on the tubular member when that sensing means produced the inspection signal, each of said storage locations including storage space for an inspection signal from a sensing means from each detector means, means for reading said storage inspection signals from said storage locations, means responsive to the read-out inspection signals for producing color coded signals wherein differently coded color coded signals correspond to a respective range of summed values of pairs of inspection signals in said storage locations, and means for visually displaying said signals on color display means in accordance with said color coding and at locations on the display means corresponding to locations on the tubular member at which the signal originated.

36. The apparatus claimed in claim 35 where each of said incremental regions has dimensions that are of the order of one-tenth inch along the length of the tubular member and 1.5° about the circumference of the member.

* * * * *